United States Patent
Verghese et al.

(10) Patent No.: US 10,388,405 B2
(45) Date of Patent: Aug. 20, 2019

(54) SYSTEMS AND METHODS FOR PREDICTING ADVERSE EVENTS AND ASSESSING LEVEL OF SEDATION DURING MEDICAL PROCEDURES

(71) Applicants: Massachusetts Institute of Technology, Cambridge, MA (US); Children's Medical Center Corporation, Boston, MA (US)

(72) Inventors: George Cheeran Verghese, Newton, MA (US); Margaret Gan Guo, San Diego, CA (US); Rebecca Mieloszyk, Redmond, WA (US); Thomas Heldt, Cambridge, MA (US); Baruch Shlomo Krauss, Brookline, MA (US)

(73) Assignees: Massachusetts Institute of Technology, Cambridge, MA (US); Children's Medical Center Corporation, Boston, MA (US)

( * ) Notice: Subject to any disclaimer, the term of this patent is extended or adjusted under 35 U.S.C. 154(b) by 278 days.

(21) Appl. No.: 15/236,193

(22) Filed: Aug. 12, 2016

(65) Prior Publication Data
US 2017/0042475 A1   Feb. 16, 2017

Related U.S. Application Data

(60) Provisional application No. 62/204,187, filed on Aug. 12, 2015.

(51) Int. Cl.
*A61B 5/083* (2006.01)
*G16C 20/30* (2019.01)
*A61B 5/00* (2006.01)

(52) U.S. Cl.
CPC ............ *G16C 20/30* (2019.02); *A61B 5/0836* (2013.01); *A61B 5/4821* (2013.01);
(Continued)

(58) Field of Classification Search
CPC ... G06F 19/704; A61B 5/0836; A61B 5/4821; A61B 5/7264; A61B 5/7271; A61B 5/746
(Continued)

(56) References Cited

U.S. PATENT DOCUMENTS

| 5,086,776 A | 2/1992 | Fowler, Jr. |
| 5,092,343 A | 3/1992 | Spitzer et al. |

(Continued)

FOREIGN PATENT DOCUMENTS

| WO | WO 2007/147505 A2 | 12/2007 |
| WO | WO-2011017778 A1 | 2/2011 |

(Continued)

OTHER PUBLICATIONS

International Search Report and Written Opinion dated Jun. 11, 2014 for Application No. PCT/US2014/021015.
(Continued)

*Primary Examiner* — Navin Natnithithadha
(74) *Attorney, Agent, or Firm* — Wolf, Greenfield & Sacks, P.C.

(57) ABSTRACT

Systems and methods are disclosed herein for quantitatively identifying a patient's sedation level and predicting adverse events, based on one or more capnograms or outputs from a pharmacokinetic, pharmacodynamic, or ventilatory model. A sensor measures a carbon dioxide concentration of air exhaled by a patient into a breath receiver. A processor processes the sensor data to generate a capnogram including one or more respiratory cycles, computes the outputs of pharmacokinetic, pharmacodynamic, or ventilatory models, and extracts one or more of the resulting features from the capnogram and pharmacokinetic, pharmacodynamic, or ventilatory model outputs. A multi-parameter metric is com-
(Continued)

puted based on the one or more extracted features and estimates the current or predicted sedation level of the patient.

15 Claims, 22 Drawing Sheets

(52) U.S. Cl.
CPC .......... *A61B 5/7264* (2013.01); *A61B 5/7271* (2013.01); *A61B 5/746* (2013.01)

(58) Field of Classification Search
USPC ................................................ 600/529–543
See application file for complete search history.

(56) References Cited

U.S. PATENT DOCUMENTS

| | | | |
|---|---|---|---|
| 5,598,508 A | 1/1997 | Goldman | |
| 6,283,923 B1 | 9/2001 | Finkelstein et al. | |
| 6,428,483 B1 | 8/2002 | Carlebach | |
| 6,540,689 B1 * | 4/2003 | Orr ........................ | A61B 5/029 600/504 |
| 6,648,833 B2 | 11/2003 | Hampton et al. | |
| 6,997,880 B2 | 2/2006 | Carlebach et al. | |
| 7,025,731 B2 * | 4/2006 | Orr ........................ | A61B 5/029 422/84 |
| 7,031,857 B2 | 4/2006 | Tarassenko et al. | |
| 7,135,001 B2 * | 11/2006 | Orr ........................ | A61B 5/029 600/526 |
| 7,398,115 B2 | 7/2008 | Lynn | |
| 7,668,579 B2 * | 2/2010 | Lynn ..................... | A61B 5/412 600/323 |
| 7,693,697 B2 | 4/2010 | Westenskow et al. | |
| 7,878,982 B2 | 2/2011 | Frank et al. | |
| 7,997,269 B2 | 8/2011 | Yudkovitch et al. | |
| 8,038,645 B2 | 10/2011 | Edginton et al. | |
| 8,147,419 B2 | 4/2012 | Krauss et al. | |
| 8,326,545 B2 | 12/2012 | Yudkovitch et al. | |
| 8,414,488 B2 | 4/2013 | Colman et al. | |
| 8,679,029 B2 | 3/2014 | Krauss et al. | |
| 8,721,542 B2 | 5/2014 | Al-Ali et al. | |
| 8,801,625 B2 * | 8/2014 | Orr ........................ | A61B 5/029 600/483 |
| 9,736,727 B2 | 8/2017 | Nagasaka et al. | |
| 2007/0010756 A1 | 1/2007 | Viertio-Oja | |
| 2007/0147505 A1 | 6/2007 | Bock | |
| 2007/0225577 A1 | 9/2007 | Mathan | |
| 2008/0009762 A1 | 1/2008 | Hampton et al. | |
| 2008/0052318 A1 | 2/2008 | Iliff et al. | |
| 2008/0082017 A1 | 4/2008 | Savic | |
| 2008/0091084 A1 | 4/2008 | Yudkovitch et al. | |
| 2010/0169063 A1 | 7/2010 | Yudkovitch et al. | |
| 2010/0212666 A1 | 8/2010 | Bouillon et al. | |
| 2011/0118619 A1 | 5/2011 | Burton et al. | |
| 2012/0016251 A1 | 1/2012 | Zhang et al. | |
| 2012/0029378 A1 | 2/2012 | Low | |
| 2012/0105485 A1 | 5/2012 | Colman et al. | |
| 2014/0155706 A1 | 6/2014 | Kochs et al. | |
| 2014/0181830 A1 | 6/2014 | Naik et al. | |
| 2014/0288440 A1 | 9/2014 | Asher et al. | |
| 2015/0038940 A1 | 2/2015 | Kreuer et al. | |
| 2015/0164412 A1 | 6/2015 | Kokko | |

FOREIGN PATENT DOCUMENTS

| | | |
|---|---|---|
| WO | WO-2012171610 A1 | 12/2012 |
| WO | WO 2014/181830 A1 | 11/2014 |

OTHER PUBLICATIONS

International Preliminary Report on Patentability dated Oct. 1, 2015 for Application No. PCT/US2014/021015.

Babik et al., Effects of respiratory mechanics on the capnogram phases: importance of dynamic compliance of the respiratory system. Critical Care. 2012;16:R177 (pp. 1-10).

Brown et al., Can quantitative capnometry differentiate between cardiac and obstructive causes of respiratory distress? Chest. Feb. 1998;113(2):323-6.

Evered et al., Can we assess asthma severity using expiratory capnography in a pediatric emergency department? Can J Emerg Med. May 2003;5(3):169-70.

Kotsiantis, Supervised machine learning: A review of classification techniques. Informatica Jan. 2007;31:249-68.

Krauss et al., Capnogram shape in obstructive lung disease. Anesth Analg. 2005;100:884-8.

Mieloszyk et al., Automated quantitative analysis of capnogram shape for COPD-Normal and COPD-CHF classification. IEEE Trans on Biomed Engineering. Dec. 2014;61(12):2882-90.

Yaron et al., Utility of the expiratory capnogram in the assessment of bronchospasm. Annals of Emergency Med. 1996;28(4):403-7.

You et al., Expiratory capnography in asthma: Evaluation of various shape indices. Eur Respir J. 1994;7:318-23.

U.S. Appl. No. 13/849,284, filed Mar. 22, 2013, Asher et al.

PCT/US2014/021045, Jun. 11, 2014, International Search Report and Written Opinion.

PCT/US2014/021015, Oct. 1, 2015, International Preliminary Report on Patentability.

International Search Report and Written Opinion dated Jan. 23, 2017 for PCT/US2016/046914, filed Aug. 12, 2016.

International Preliminary Report on Patentability dated Feb. 22, 2018 for Application No. PCT/US2016/046914.

Baxt, Improving the accuracy of an artificial neural network using multiple differently trained networks. Neural Computation. 1995;4(5):772-80.

\* cited by examiner

2200

2202
IDENTIFY SEDATION AGENT INFORMATION INCLUDING AT LEAST ONE OF A TIME, A TYPE, AND AN AMOUNT OF SEDATION AGENT ADMINISTERED TO A PATIENT

2204
COMPUTE, USING A PHARMACOKINETIC MODEL, A CONCENTRATION OF SEDATION AGENT IN THE BODY OF THE PATIENT BASED ON THE SEDATION AGENT INFORMATION

2206
COMPUTE A FIRST PREDICTED SEDATION LEVEL BASED ON THE COMPUTED CONCENTRATION

2208
SELECT A CANDIDATE DOSE OF SEDATION AGENT BASED ON THE SEDATION AGENT INFORMATION

2210
COMPUTE A SECOND PREDICTED SEDATION LEVEL BASED ON THE CANDIDATE DOSE OF SEDATION AGENT

2212
PROVIDE, TO A DISPLAY, AT LEAST ONE OF THE COMPUTED CONCENTRATION AND THE FIRST PREDICTED SEDATION LEVEL AND AT LEAST ONE OF THE CANDIDATE DOSE OF SEDATION AGENT AND THE SECOND PREDICTED SEDATION LEVEL

FIG. 22

SYSTEMS AND METHODS FOR PREDICTING ADVERSE EVENTS AND ASSESSING LEVEL OF SEDATION DURING MEDICAL PROCEDURES

CROSS-REFERENCE TO RELATED APPLICATIONS

This application claims priority under 35 U.S.C. § 119(e) to U.S. Provisional Application No. 62/204,187, filed Aug. 12, 2015, and is related to U.S. application Ser. No. 13/849,284, filed Mar. 22, 2013, each of which is incorporated herein by reference in its entirety for all purposes. This application is also related to co-pending PCT Application No. PCT/US2016/046914, filed Aug. 12, 2016, which is hereby incorporated herein by reference in its entirety for all purposes.

TECHNICAL FIELD

In general, this disclosure relates to systems and methods for monitoring procedural sedation, and to the use of quantitative capnogram features or models of pharmacokinetics, pharmacodynamics, or ventilation for this purpose.

BACKGROUND

Procedural sedation is a standard technique used to manage acute pain and anxiety for spontaneously breathing adults and children undergoing medical procedures outside the operating room and intensive care unit. Procedural sedation differs from general anesthesia which suppresses central nervous system activity and results in unconsciousness and lack of sensation. Monitoring of anesthesia is described generally in PCT Patent Publication WO 2012/171610 by Kochs et al., U.S. Pat. No. 8,326,545 by Yudkovitch et al., U.S. Pat. No. 7,878,982 by Frank et al., U.S. Pat. No. 7,997,269 by Yudkovitch et al., US Patent Publication No. 2011/0118619 by Burton et al., WO 2011/017778 by Burton, U.S. Pat. No. 7,693,697 by Westenskow et al., US Patent Publication No. 2010/0169063 by Yudkovitch et al., and US Patent Publication No. 2008/0091084 by Yudkovitch et al., all of which are incorporated herein by reference.

In clinical settings where patients are sedated for medical procedures, i.e., undergoing procedural sedation, clinicians rely on qualitative methods to assess sedation state and track changes in the level of sedation of the patient, as well as any abnormal respiratory reaction. For example, clinicians may tap a patient on the shoulder or try to communicate with the patient in order to use degree of responsiveness as a surrogate measure for sedation level. These qualitative methods may be insufficient to detect patient oversedation, which can lead to respiratory compromise, or patient undersedation, which can result in unnecessary pain or anxiety. These qualitative approaches are limited and subjective as they are dependent on each clinician's acumen and experience in assessing sedation level, and therefore cannot be transferred from one clinical setting to another. Existing methods of monitoring in procedural sedation are not quantitative in nature, and, in particular, underutilize the capabilities of capnography and pharmacokinetic/pharmacodynamic modeling. The assessment of patient state during procedural sedation using electroencephalogram (EEG) signals is described in US Patent Publication No. 2007/0010756 by Viertio-Oja et al. However, EEG-derived sedation levels such as the bispectral index have not proven useful for assessing the lighter levels of sedation attained during procedural sedation, and are not used in current procedural sedation practice. Additionally, EEG is not generally monitored during procedural sedation. In the context of procedural sedation, US Patent App. Pub. No. 2010/0212666 by Bouillon et al. describes a controller apparatus and drug delivery system. The aforementioned applications are incorporated herein by reference as prior art that describe the use of pharmacokinetic models in the procedural sedation environment. However, both of these patent applications describe the use of pharmacokinetic model outputs to administer sedative agents in a closed-loop system. The system and methods proposed here instead claim the use of pharmacokinetic model outputs to guide drug titration with clinician input. Compartmental concentrations and/or corresponding sedation levels estimated by the pharmacokinetic or pharmacodynamic models will be presented to a clinician and serve as a recommendation or guidance system.

Capnography refers to the noninvasive measurement of the concentration of carbon dioxide, [$CO_2$], in exhaled breath. Carbon dioxide is a byproduct of tissue metabolism. The [$CO_2$] in exhaled breath can be measured noninvasively as a function of time or of volume. These measurement processes are respectively called time-based and volumetric capnography. Capnography monitors can be found in every properly equipped operating room, intensive care unit, and emergency department, as monitoring [$CO_2$] in patients is an essential aspect of modern respiratory care, for example, to confirm successful endotracheal intubation. The waveform produced during capnography is called a capnogram and reflects underlying respiratory dynamics. However, currently only a small portion of the wealth of information contained in the capnogram is extracted and processed for use by clinicians.

Pharmacokinetic modeling describes the estimation of relevant physiological concentrations following drug administration. Pharmacodynamic modeling refers to the mapping of physiological drug concentrations to a predicted effect. Both pharmacokinetic and pharmacodynamic models have been used to estimate resulting physiological concentrations and effects following the administration of sedation agents, including propofol[1] and ketamine[2]. However, the resulting effect outputs of pharmacodynamic models have typically been correlated with the bispectral index[3], an EEG-derived quantity that is not found to be useful at the lighter levels of sedation experienced during procedural sedation[4]. Pharmacokinetic and pharmacodynamic models are particular to the type of drug administered, and model parameters vary due to patient-specific covariates such as age and weight. Such models typically contain multiple compartments that describe the differing drug metabolism and equilibration across various tissues and organ systems.

[1] Schüttler, Jürgen, and Harald Ihmsen "Population Pharmacokinetics of Propofol: A Multicenter Study." The Journal of the American Society of Anesthesiologists 92.3 (2000): 727-738.
[2] Herd, David W., et al. "Investigating the pharmacodynamics of ketamine in children." Pediatric Anesthesia 18.1 (2008): 36-42.
[3] Lysakowski, Christopher, et al. "Bispectral and spectral entropy indices at propofol-induced loss of consciousness in young and elderly patients." British journal of anaesthesia 103.3 (2009): 387-393.
[4] Gill, Michelle, Steven M. Green, and Baruch Krauss. "A study of the bispectral index monitor during procedural sedation and analgesia in the emergency department." Annals of emergency medicine 41.2 (2003): 234-241.

SUMMARY

Systems and methods are disclosed herein for automatically providing a quantitative assessment of a physiological state of a patient during procedural sedation. In particular, a system for automatically providing a quantitative assessment of a physiological state of a patient during procedural sedation is described. The system comprises a breath receiver, a sensor, and a processor. The breath receiver is in fluid communication with a patient undergoing procedural sedation. The sensor is coupled to the breath receiver and used for measuring a carbon dioxide concentration in air captured by the breath receiver. The processor is configured to process data from the sensor to generate, in real time, a capnogram associated with the patient, the capnogram including one or more respiratory cycles, extract, in real time, one or more features from the capnogram that are indicative of physiological state of the patient, compute, in real time, a metric indicative of a physiological state of the patient based on the one or more features from the capnogram, compute a degree of confidence in the physiological state indicated by the metric, determine a baseline value of the metric for the patient, the baseline value corresponding to a baseline state of the patient before procedural sedation begins, and monitor, in real time, a value of the metric relative to the baseline value and an associated physiological state.

In one implementation, the processor is further configured to detect in real time a change in a value of the metric over at least two respiratory cycles, and determine in real time a change in the real time physiological state of the patient based on the change in the value of the metric.

In one implementation, the processor is further configured to correlate the physiological state of the patient with one or more physiological data or indicators to determine the accuracy of the determined change in physiological state.

In one implementation, the one or more physiological data or indicators are input to a clustering technique, including at least one of physiological data provided by the user, outputs from at least one of a pharmacokinetic, pharmacodynamic, and ventilatory model, and a score on a qualitative sedation scoring scheme.

In one implementation, the extracting the one or more features includes fitting a portion of the capnogram to a parameterized function In one implementation, the one or more features include a measure of periodicity of the capnogram.

In one implementation, the one or more features include the output of at least one of a pharmacokinetic model, a pharmacodynamics model, and a ventilatory model.

In one implementation, the one or more features that are indicative of physiological states of the patient include a terminal value of CO2 on exhalation, an end-exhalation slope, and a ratio of an intermediate exhalation slope over an initial exhalation slope.

In one implementation, the processor is further configured to use, in real time, a clustering technique to determine clusters of the one or more features indicative of the physiological states of the patient.

In one implementation, the clustering technique is a k-means technique, with a number "k" of clusters corresponding to a number of sedation states for the patient.

In one implementation, the clustering technique is a technique with a variable number of clusters.

In one implementation, the metric is a multi-parameter metric, where the multi-parameter metric indicates a separation from a cluster centroid.

In one implementation, a closest centroid, as determined by the multi-parameter metric, is indicative of the physiological state of the patient.

In one implementation, a separation from a nearest centroid relative to a separation from a next-closest centroid is indicative of a degree of confidence in the physiological state of the patient.

In one implementation, the physiological state of the patient pertains to a sedation level.

According to another aspect, the disclosure relates to a system for guiding procedural sedation. In particular the system comprises at least one processor. The at least one processor is configured to identify sedation agent information including at least one of a time, a type, and an amount of sedation agent administered to a patient, compute, using a pharmacokinetic model, a concentration of sedation agent in the body of the patient based on the sedation agent information, compute a first predicted sedation level based on the computed concentration, select a candidate dose of sedation agent based on the sedation agent information, compute a second predicted sedation level based on the candidate dose of sedation agent, and provide, to a display, at least one of the computed concentration and the first predicted sedation level and at least one of the candidate dose of sedation agent and the second predicted sedation level.

In one implementation, the at least one processor is further configured to select a pharmacodynamics model, wherein the pharmacodynamic model is used to estimate an effect resulting from the computed concentration.

In one implementation, the at least one processor is further configured to compute the first predicted sedation level based on the computed concentration and the pharmacodynamics model.

In one implementation, the at least one processor is further configured to alert a user when the computed concentration exceeds a first concentration threshold or is below a second concentration threshold.

In one implementation, the at least one processor is further configured to alert a user when the first predicted sedation level exceeds a first sedation threshold or is below a second sedation threshold.

In one implementation, the system further comprises an interactive bedside monitor configured to record sedation agent information.

In one implementation, the pharmacokinetic model and the pharmacodynamic model are compartmental models.

In one implementation, the pharmacokinetic model includes parameters based on at least one of age, weight, height, lean body mass, gender, and procedure type.

In one implementation, the computed concentration comprises at least one of a plasma concentration and an effect-site concentration.

In one implementation, alerting the user when the computed concentration exceeds a first concentration threshold or is below a second concentration threshold is based on an emergence threshold of the sedation agent.

In one implementation, the display continuously updates the graphic presentation of the computed concentration.

According to another aspect, the disclosure relates to a method for automatically providing a quantitative assessment of a physiological state of a patient during procedural sedation. Data indicating a carbon dioxide concentration in air captured by a breath receiver is measured by a sensor coupled to the breath receiver and received by a processor. Data from the sensor is processed to generate, in real time, a capnogram associated with the patient, the capnogram including one or more respiratory cycles. One or more features from the capnogram that are indicative of a physiological state of the patient are extracted in real time. a metric indicative of a physiological state of the patient is computed, in real time, based on the one or more features from the capnogram. A degree of confidence in the physiological state indicated by the metric is computed. A baseline value of the metric for the patient is determined, the baseline value corresponding to a baseline state of the patient before procedural sedation begins. A value of the metric relative to the baseline value and an associated physiological state are monitored in real time.

According to another aspect, the disclosure relates to a method for automatically guiding procedural sedation. Sedation agent information including at least one of a time, a type, and an amount of sedation agent administered to a patient is identified. A concentration of sedation agent in the body of the patient is computed based on the sedation agent information. A first predicted sedation level is computed based on the computed concentration. A candidate dose of sedation agent is selected based on the sedation agent information. A second predicted sedation level is computed based on the candidate dose of sedation agent. At least one of the computed concentration and the first predicted sedation level and at least one of the candidate dose of sedation agent and the second predicted sedation level are provided to a display

BRIEF DESCRIPTION OF THE DRAWINGS

The above and other features of the present disclosure, including its nature and its various advantages, will be more apparent upon consideration of the following detailed description, taken in conjunction with the accompanying drawings in which:

FIG. 22 is a flow chart depicting a method for automatically guiding procedural sedation, according to an illustrative implementation of the disclosure.

DETAILED DESCRIPTION

Figure 1:
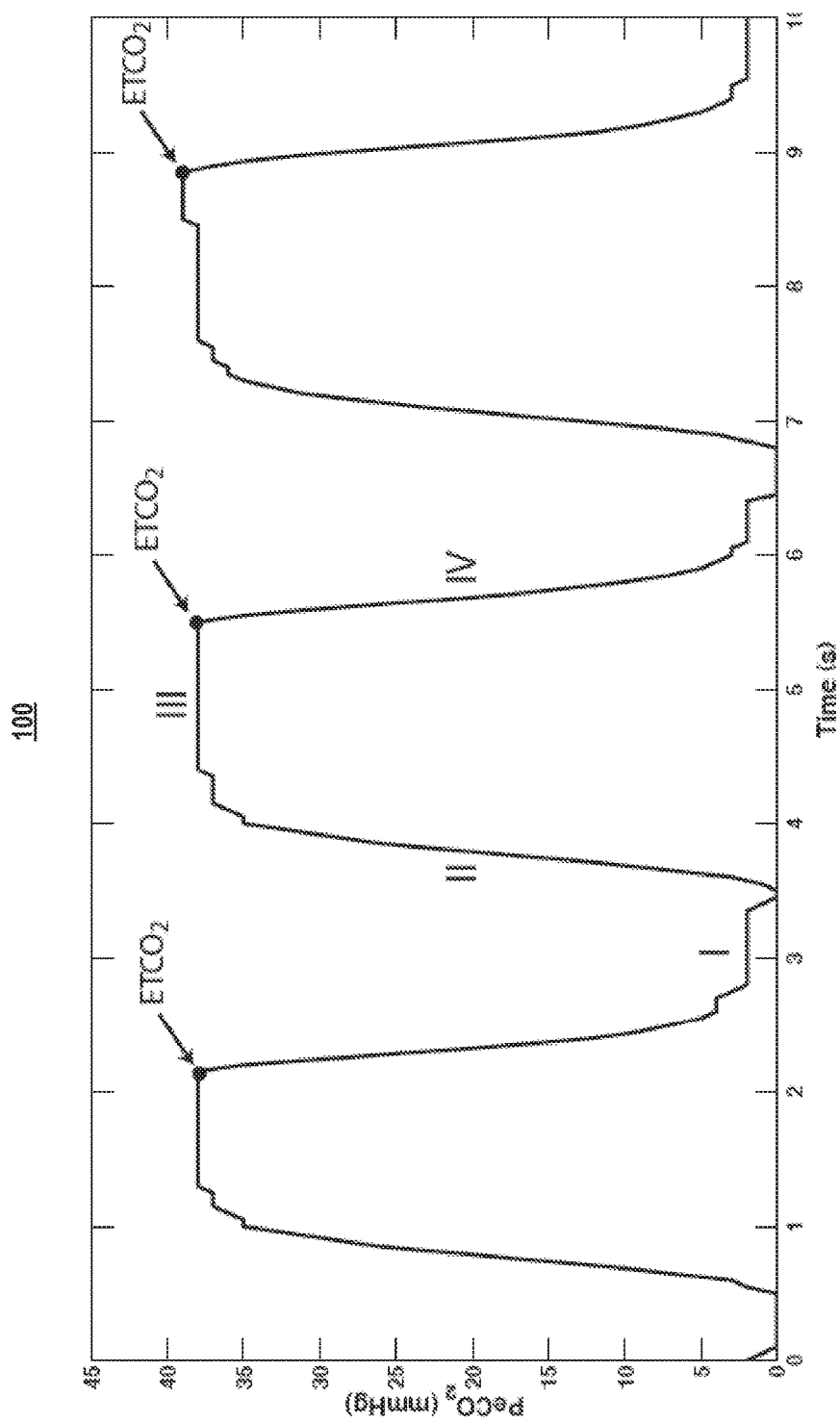
FIG. 1 is a diagram of a capnogram, according to an illustrative implementation of the disclosure.

To provide an overall understanding of the systems and methods described herein, certain illustrative embodiments will now be described, including a system for monitoring sedation state and detecting adverse events during procedural sedation, using capnograms, pharmacokinetic, pharmacodynamic, or ventilatory model outputs, or other physiological or demographic data. However, it will be understood by one of ordinary skill in the art that the systems and methods described herein may be adapted and modified as is appropriate for the application being addressed and that the systems and methods described herein may be employed in other suitable applications, and that such other additions and modifications will not depart from the scope thereof. Generally, the computerized systems described herein may comprise one or more local or distributed engines, which include a processing device or devices, such as a computer, microprocessor, logic device or other device or processor that is configured with hardware, firmware, and software to carry out one or more of the computerized methods described herein.

The present disclosure provides systems and methods for providing sedation state monitoring using one or more of capnograms, pharmacokinetic models, pharmacodynamic models, ventilatory model outputs, and additional demographic and physiological data when available. Quantitative analysis of the capnogram allows capnography to be used as a monitoring tool, and a capnography-based monitoring system that quantitatively indicates within a procedure different sedation levels of a patient, for example corresponding to different procedural sedation events (including drug administration and clinical interventions), which constitutes a significant improvement in monitoring. Several factors make capnography an attractive respiratory monitoring tool. First, as a measure of ventilation, it accurately reflects underlying pulmonary physiology and pathophysiology. Second, capnography is an effort-independent measurement that simply entails breathing normally through a nasal cannula, mask, or mouthpiece. Third, with mathematical modeling and computational analysis, capnography provides an objective test: rather than relying on subjective qualitative observation for determining a patient's physiological state in response to a level of sedation, capnography allows for a quantitative sedation level assessment. Pharmacokinetic and pharmacodynamic modeling map drug administration inputs to predicted compartmental concentrations and effects, with parameters that depend on patient-specific attributes such as age, gender, weight, height, and lean body mass. The model structure and parameter values are based on measured plasma concentrations in controlled human-subject experiments following procedural sedation agent administration. Pharmacokinetic and pharmacodynamic models quantitatively describe the effects of administered sedation agents. In particular, the proposed monitoring system helps reduce subjectivity from clinical decision making with respect to individual sedation and respiratory state. The present disclosure describes, in one implementation, a simplified one-compartment pharmacokinetic model, with reference to FIG. 19, that can often suffice to reliably model the plasma concentrations of sedation agents over the time course relevant for procedural sedation. In multi-compartment models, the effect-site sedation agent concentration is observed to closely mirror that of the plasma, as discussed with reference to FIG. 20. These models are applied to the clinician guidance and recommended titration of sedation agent during procedural sedation.

Presently, many procedures are being performed with procedural sedation, and outside of the operating room or intensive care unit. Following the 2011 guidelines of the American Society of Anesthesiologists (ASA), capnography has become a standard of care for ventilation monitoring of sedated patients, providing the earliest detection of respiratory compromise.[5] Monitoring patient vital signs during procedural sedation, with a particular emphasis on respiratory status, provides critical, immediate information on patient well-being. However, although the goal of procedural sedation is to provide adequate sedation for the procedure, the line between adequate sedation and oversedation, and, similarly, the line between adequate sedation and undersedation, is very narrow and can be difficult to recognize. Oversedation carries the risk of respiratory compromise and harm to the patient. Undersedation carries the risk of patient pain and physical and emotional discomfort.

[5] See American Society of Anesthesiologists. "ASA Standards for 2011—Capnography," and see Krauss B. Hess DR. Capnography for Procedural Sedation and Analgesia in the Emergency Department. *Annals of Emergency Medicine* 2007; 50: 172-181, both of which are herein incorporated by reference in their entirety.

As referred to herein, the term capnography is the non-invasive measurement of exhaled carbon dioxide concentration, and the term capnogram denotes the resulting waveform. As referred to herein, a breath receiver is a device such as a cannula, mask, mouthpiece, or any other device for capturing exhaled air from a patient. A breath receiver may be connected to a sensor which measures the carbon dioxide concentration in the captured exhaled air, and generates a corresponding recordable signal, for example to display a capnogram.

As defined herein, a pharmacokinetic model includes any model that takes as input procedural sedation agent type, administration times, and dosing, and predicts as output the concentration of sedation agent in various compartments that may or may not be physiologically based.

As defined herein, a pharmacodynamic model includes any model that takes as input compartmental concentrations of procedural sedation agent and outputs a predicted sedation level or depth of hypnosis.

As defined herein, a clustering technique is any unsupervised or semi-supervised or supervised learning technique that determines associations between specific capnogram parameters or metrics and a specified or inferred number of underlying sedation states, represented by clusters, which may normally number from two to ten. The determination of such associations, to guide the construction and labeling of clusters, may involve using no labeled data (for unsupervised learning), or using some labeled data (for semi-supervised learning), or using extensive labeled data (for supervised learning). In a non-limiting example, an unsupervised clustering technique may be a hierarchical clustering technique or a k-means technique, where k is the number of sedation states.

As defined herein, a clustering technique may be causal or non-causal. A causal clustering technique may use prior information to guide later computations: a causal clustering technique may be run in real time on a sequentially increasing number of exhalations. A non-causal clustering technique may be run a-posteriori on a data set containing a finite number of exhalations.

As defined herein, a sedation level is a level of sedation for a patient, i.e., an indication of the patient's awareness or perception of his/her surroundings and responsiveness to external stimuli. As defined herein, a respiratory cycle is defined as the period of time between two exhalations, measured from the beginning of alveolar gas exhalation in one breath to the corresponding beginning of alveolar gas exhalation for the next breath.

As defined herein, a clinical intervention may include any of the following non limiting events: an airway repositioning, a verbal stimulation, a tactile stimulation, and an administration of supplemental oxygen. As described herein, an adverse event is an event that negatively affects the patient. For example, an adverse event may be a patient feeling unnecessary pain. As a further example, an adverse event may be apnea. Apnea during a procedure (such as cardioversion, colonoscopy, fracture reduction, abscess incision and drainage, or laceration repair) may affect the recovery of the patient. If the apnea leads to hypoxia, the patient's condition may become life threatening.

FIG. 1 is a diagram 100 of a normal time-based capnogram with four phases (labeled I-IV in FIG. 1). Each phase of the capnogram corresponds to a specific segment of the respiratory cycle. Dead-space ventilation occurs during the first phase of exhalation (I), the start of alveolar gas exhalation during the second phase (II), an alveolar plateau during the third phase (III), and an inspiratory downstroke constitutes the fourth phase (IV), to complete the waveform. The terminal value of alveolar [CO2] during exhalation is defined as the End-Tidal CO2 (ETCO2), the maximum concentration of CO2 ([CO2]) in each breath.

The capnogram contains important information about metabolic and cardiorespiratory function. The instantaneous respiratory rate is calculated as the reciprocal of the time from the beginning of alveolar gas exhalation (the start of phase two) on one breath to the corresponding point of the next, while the amplitude of the capnogram at the end of exhalation, the ETCO2 value, reflects arterial [CO2]. These two parameters are important clinically because they capture key features of the cardiorespiratory function, but the entire waveform contains more information than can be aggregated by these two summary statistics. For example, parameters such as exhalation duration, slopes at various phases of the exhalation, and times spent in various concentration intervals may provide additional information.

An intent of the present disclosure is to provide a quantitative and automated assessment of a capnogram to correctly assess and detect a physiological state of a patient undergoing procedural sedation, e.g., to assess and detect a baseline level of sedation and changes in level of sedation relative to the baseline for this patient. Capnogram shape is not easy to characterize by visual inspection, making it difficult for a physician to make an objective diagnosis of the patient's physiological state by simply observing the capnogram. One intent of the present disclosure is to quantitatively and objectively correlate features of monitoring data, in particular capnogram data, with physiological processes that relate to sedation and respiratory state, to determine a physiological state of the patient.

The outputs of pharmacokinetic models used to estimate plasma or effect-site concentrations can be informative in predicting depth of sedation. In referring to procedural sedation agents, the effect-site can be identified as the brain, cerebrospinal fluid, or other sites within the central nervous system. Pharmacodynamic models may also be employed to map pharmacokinetic outputs to an estimated effect, which can be used to assess sedation level.

In current clinical practice, the outputs of pharmacokinetic/pharmacodynamic models are not examined during the course of procedural sedation. However, these models are highly descriptive in their identification of compartmental concentrations and predicted effects following sedation agent administration. Such models have practical use in guiding the appropriate titration of sedative agent. In one embodiment, a simplified pharmacokinetic model is proposed and discussed with reference to FIG. 19. This simplified model takes as input the sedation agent administration amounts and times. The model then outputs a predicted plasma concentration according to the first-order differential equation discussed with reference to FIG. 19. In this embodiment, age- and gender-specific parameters required for estimation include a volume of distribution, $V_1$, and a rate constant, $k_{10}$, describing clearance from the plasma. These parameters may be estimated using literature values or calculated experimentally from representative patient populations.

Another intent of the present disclosure is to build patient-specific models of the pharmacokinetics and pharmacodynamics of procedural sedation agent action, and models relating ventilation status to exhaled [$CO_2$], in order to generate additional features for clustering, and to enable proactive warnings for impending adverse respiratory events. The outputs of such models can be used in isolation or in conjunction with one or more of capnography and other monitoring data as inputs to a clustering technique. Yet another intent of the present disclosure is to develop a pattern-recognition based method for distinguishing levels of sedation and guiding titration of sedative drugs in a procedure-specific and patient-specific manner. The systems and methods described herein demonstrate the monitoring and diagnostic capabilities of capnography and of real-time simulation of pharmacokinetic/pharmacodynamics models.

The systems and methods of the present disclosure may be described in more detail with reference to FIGS. 2-22. More particularly, an exemplary diagram tracking the evolution of the sedation level of a patient is described with reference to FIG. 2. Various key features of a capnogram are discussed in relation to FIGS. 3-5 and 7-8. The system, as exemplified in FIG. 6, may provide a process for extracting capnogram features as described with reference to flow charts in FIGS. 9-10. Additional capnogram data, including extracted features and the physiological states determined by computing a metric, are described with reference to FIGS. 11-14. Pharmacokinetic and pharmacodynamics modeling are discussed with reference to FIGS. 15-20. FIG. 21 describes a method for automatically providing a quantitative assessment of a physiological state of a patient during procedural sedation, according to an illustrative implementation of the disclosure. FIG. 22 describes a method for automatically guiding procedural sedation, according to an illustrative embodiment of the disclosure.

Figure 2:
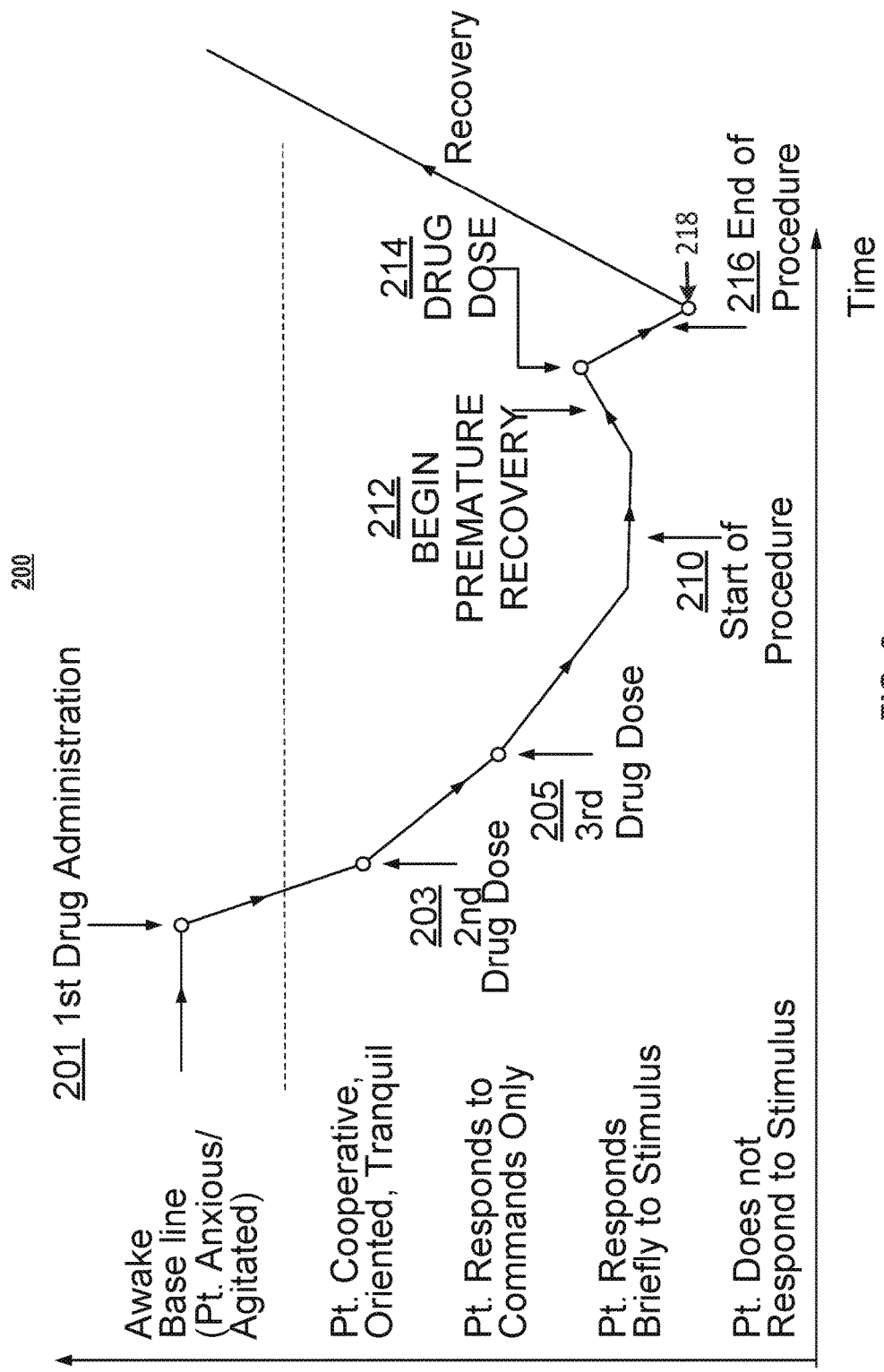
FIG. 2 is a diagram of exemplary physiological states during procedural sedation, according to an illustrative implementation of the disclosure.

FIG. 2 is a diagram of exemplary physiological states during procedural sedation, according to an illustrative implementation of the disclosure. FIG. 2 shows a graph of sedation state plotted against time, during a procedure. A pathway with elements 201, 203, 205, 210, 212, 214, 216, and 218 indicates the changes in sedation level for a patient undergoing an exemplary procedural sedation. The patient may begin in an exemplary baseline state and may be anxious or agitated ahead of his/her procedure. At 201, the patient may be given sedatives or narcotics, a first drug administration, which changes the sedation state of the patient to a more cooperative, tranquil state, e.g., a "deeper" sedation state. At 203 and 205, the patient may be given additional drug doses, which impact his/her sedation state, such that the patient responds to commands only, and subsequently responds only briefly to stimuli. At 210, the physician may start the procedure. The physician may decide to start the procedure once the patient is below a certain responsiveness threshold, indicated for example by the dashed line in FIG. 2. This threshold level may vary depending on the preferences of the physician, and the procedure type, or the methods used to assess sedation state. At 212, depending on health characteristics and risk factors of the patient, the patient may begin a premature recovery, reaching a lighter level of sedation, indicated by a lightening of the sedation state between 212 and 214. At 214, a physician may detect the premature recovery and administer an additional drug dose, just before the end of the procedure at 216. The drug dose provides additional sedation at 218, and the patient may then begin recovery back to the baseline state. However, the additional drug dose administered at 214 may also in some instances lead to oversedation, leaving the patient in a deeper sedation state, where the patient may suffer an adverse respiratory event, such as an obstruction or hypoxia.

Figure 3:
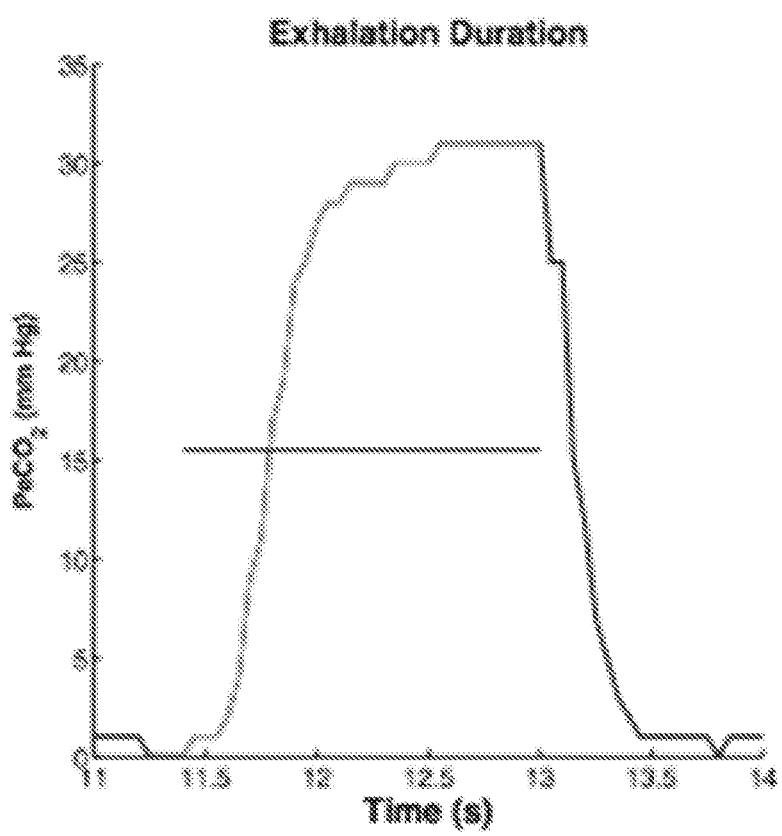
FIG. 3 is a diagram of a capnogram, including a feature of exhalation duration, according to an illustrative implementation of the disclosure.

Referring now to FIG. 3, a diagram 300 shows a capnogram, including a feature of exhalation duration. Exhalation duration is measured from the initial increase in [CO2] until the first drop in [CO2] after attainment of ETCO2. Exhalation duration is an important determinant of respiratory rate, is prolonged in respiratory depression during procedural sedation. Exhalation duration is therefore an important parameter in determining the physiological state of a patient.

Figure 4:
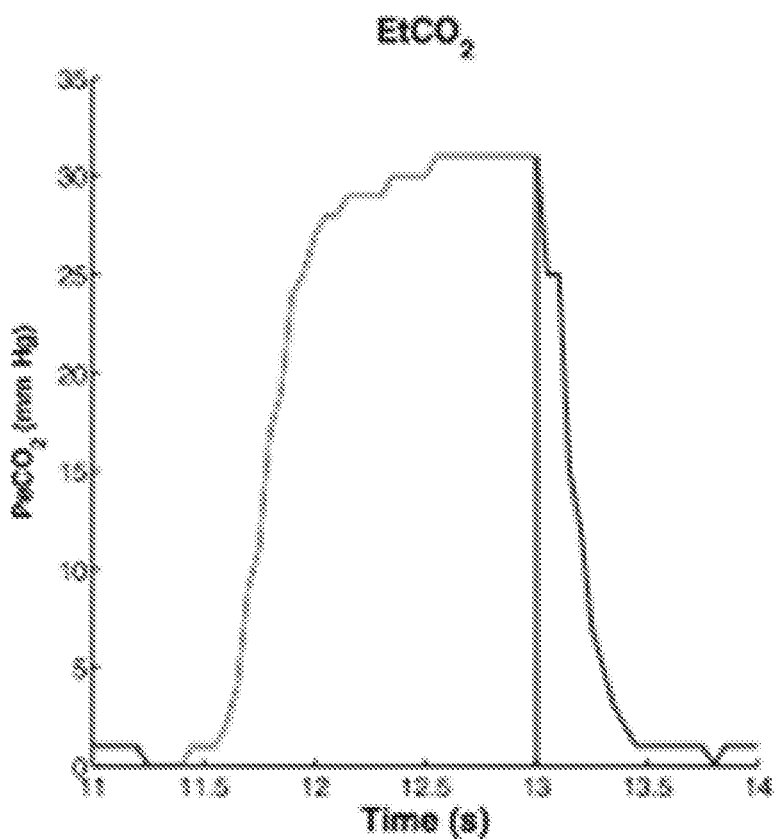
FIG. 4 is a diagram of a capnogram, including a feature of a terminal value on exhalation, according to an illustrative implementation of the disclosure.

Referring now to FIG. 4, a diagram 400 shows a capnogram, including a feature of a terminal value on exhalation. The terminal value on exhalation is captured just before the capnogram begins decreasing and is labeled as the ETCO2 value. For example, during obstructed breathing, patients are generally seen to exhibit high ETCO2 values. ETCO2 is therefore an important parameter in determining the physiological state of a patient.

Figure 5:
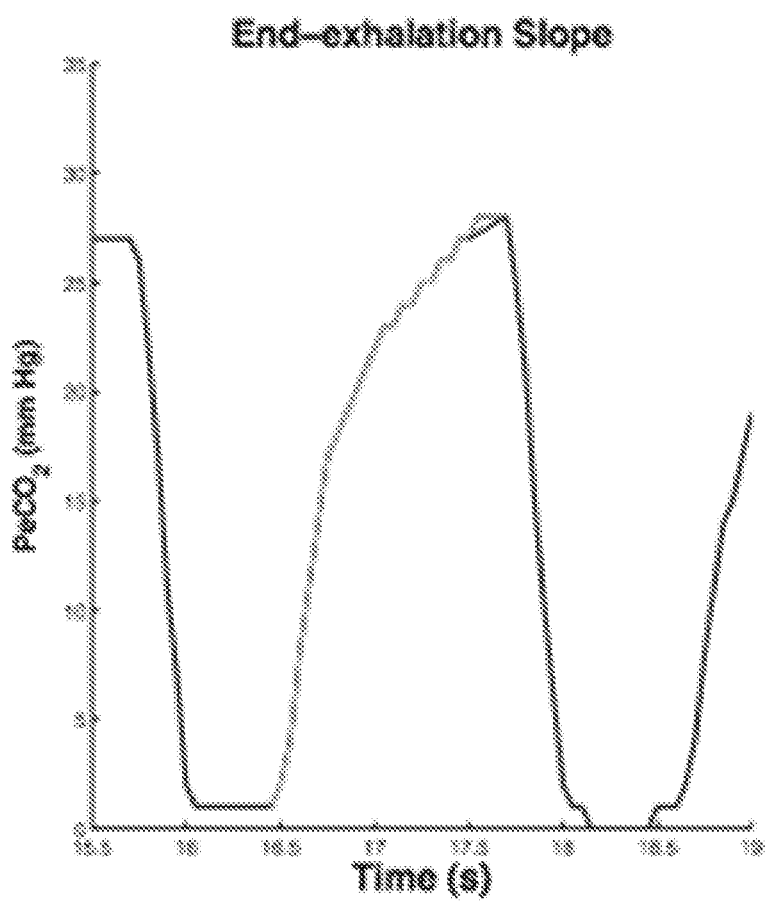
FIG. 5 is a diagram of a capnogram, including a feature of a slope at an end of an exhalation, according to an illustrative implementation of the disclosure.

Referring now to FIG. 5, a diagram 500 shows a capnogram, including a feature of a slope at an end of an exhalation, S3. This slope reflects the degree of completion of CO2 exhalation at the beginning of the next inhalation. In an example, to extract the end-exhalation slope, the system of the present disclosure implements a linear regression over the last fifth of the capnogram exhalation. The slope of this regression line is then taken as the end-exhalation slope. Because normal breathing results in a relatively flat alveolar plateau and obstructed breathing yields a more rounded or "shark fin" shape, the end-exhalation slope feature is especially useful in distinguishing obstructed from normal exhalations. Both ETCO2 and S3 have previously been found useful in pulmonary disease screening and diagnosis.[6] ETCO2 and S3 are therefore important parameters in determining the physiological state of a patient.

[6] See R. J. Mieloszyk et al. "Automated quantitative analysis of capnogram shape for COPD—Normal and COPD—CHF classification," *IEEE Trans. Biomed. Eng.*, vol. 61, no. 12, pp. 2882-2890, 2014, which is herein incorporated by reference in its entirety.

Figure 6:
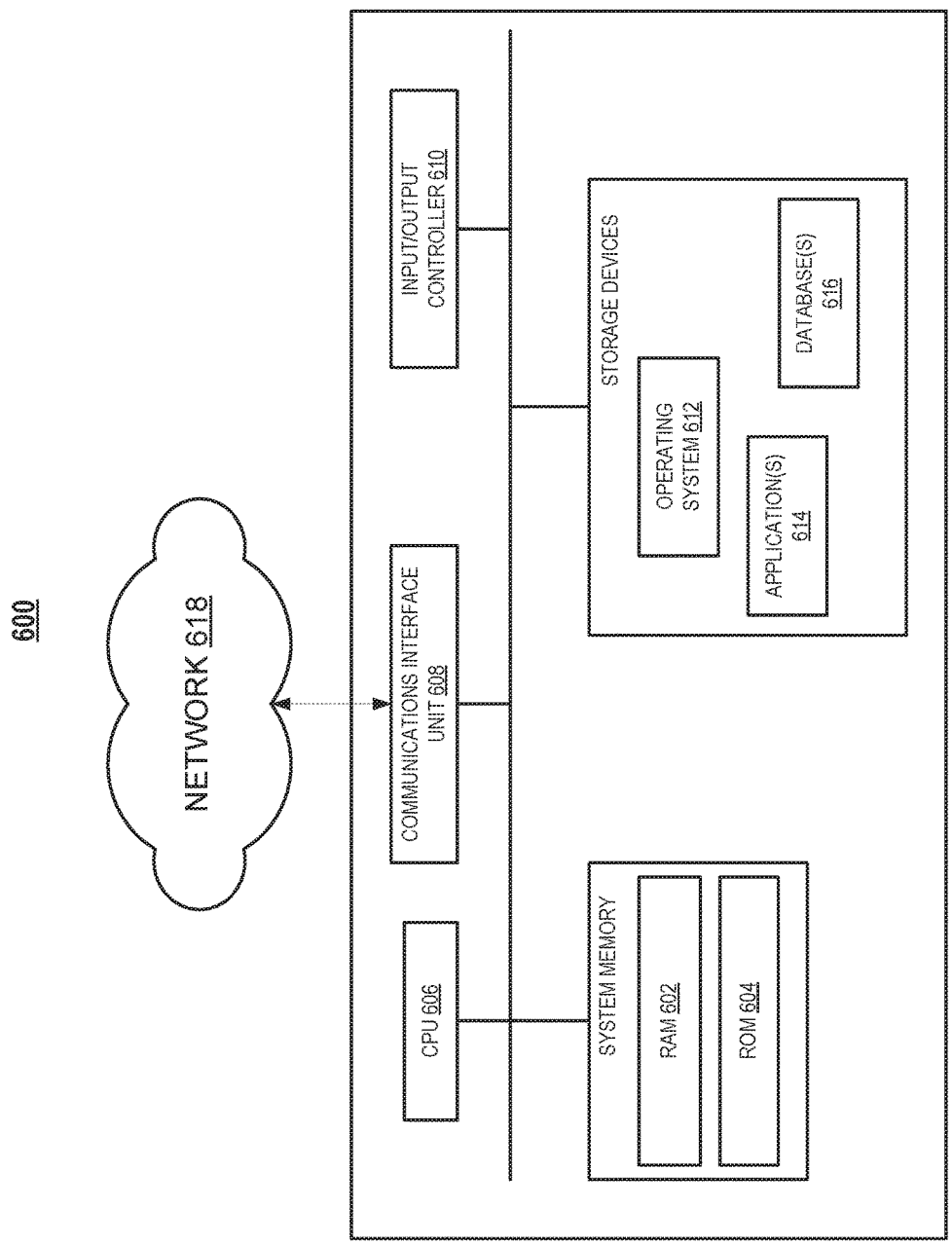
FIG. 6 is a block diagram of a computing device for performing any of the processes described herein, according to an illustrative implementation of the disclosure.

FIG. 6 is a block diagram of a computing device for performing any of the processes described herein, according to an illustrative implementation of the disclosure. Each of the components of these systems may be implemented on one or more computing devices 600. In certain aspects, a plurality of the components of these systems may be included within one computing device 600. In certain implementations, a component and a storage device may be implemented across several computing devices 600.

The computing device 600 comprises at least one communications interface unit, an input/output controller 610, system memory, and one or more data storage devices. The system memory includes at least one random access memory (RAM 602) and at least one read-only memory (ROM 604). All of these elements are in communication with a central processing unit (CPU 606) to facilitate the operation of the computing device 600. The computing device 600 may be configured in many different ways. For example, the computing device 600 may be a conventional standalone computer or, alternatively, the functions of computing device 600 may be distributed across multiple computer systems and architectures. In FIG. 6, the computing device 600 is linked, via network or local network, to other servers or systems.

The computing device 600 may be configured in a distributed architecture, wherein databases and processors are housed in separate units or locations. Some units perform primary processing functions and contain, at a minimum, a general controller or a processor and a system memory. In distributed architecture implementations, each of these units may be attached via the communications interface unit 608 to a communications hub or port (not shown) that serves as a primary communication link with other servers, client or user computers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP.

The CPU 606 comprises a processor, such as one or more conventional microprocessors and one or more supplementary co-processors such as math co-processors for offloading workload from the CPU 806. The CPU 606 is in communication with the communications interface unit 608 and the input/output controller 610, through which the CPU 606 communicates with other devices such as other servers, user terminals, or devices. The communications interface unit 608 and the input/output controller 610 may include multiple communication channels for simultaneous communication with, for example, other processors, servers or client terminals in the network 618.

The CPU 606 is also in communication with the data storage device. The data storage device may comprise an appropriate combination of magnetic, optical or semiconductor memory, and may include, for example, RAM 602, ROM 604, flash drive, an optical disc such as a compact disc or a hard disk or drive. The CPU 606 and the data storage device each may be, for example, located entirely within a single computer or other computing device; or connected to each other by a communication medium, such as a USB port, serial port cable, a coaxial cable, an Ethernet cable, a telephone line, a radio frequency transceiver or other similar wireless or wired medium or combination of the foregoing. For example, the CPU 606 may be connected to the data storage device via the communications interface unit 608. The CPU 606 may be configured to perform one or more particular processing functions.

The data storage device may store, for example, (i) an operating system 612 for the computing device 600; (ii) one or more applications 614 (e.g., computer program code or a computer program product) adapted to direct the CPU 606 in accordance with the systems and methods described here, and particularly in accordance with the processes described in detail with regard to the CPU 606; or (iii) database(s) 616 adapted to store information that may be utilized to store information required by the program.

The operating system 612 and applications 614 may be stored, for example, in a compressed, an uncompiled and an encrypted format, and may include computer program code. The instructions of the program may be read into a main memory of the processor from a computer-readable medium other than the data storage device, such as from the ROM 604 or from the RAM 602. While execution of sequences of instructions in the program causes the CPU 606 to perform the process steps described herein, hard-wired circuitry may be used in place of, or in combination with, software instructions for implementation of the processes of the present disclosure. Thus, the systems and methods described are not limited to any specific combination of hardware and software.

Suitable computer program code may be provided for performing one or more functions in relation to performing classification of physiological states based on capnograms as described herein. The program also may include program elements such as an operating system 612, a database management system and "device drivers" that allow the processor to interface with computer peripheral devices (e.g., a video display, a keyboard, a computer mouse, etc.) via the input/output controller 610.

The term "computer-readable medium" as used herein refers to any non-transitory medium that provides or participates in providing instructions to the processor of the computing device 600 (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer can read.

Various forms of computer readable media may be involved in carrying one or more sequences of one or more instructions to the CPU 606 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device 600 (e.g., a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

A variety of features and parameters may be extracted from capnograms, as described for example in U.S. Pat. No. 6,428,483 by Carlebach et al., U.S. Pat. No. 8,679,029 by Krauss, and U.S. Pat. No. 9,721,542 by Al-Ali, all of which are incorporated herein by reference in their entirety.

Figure 7:
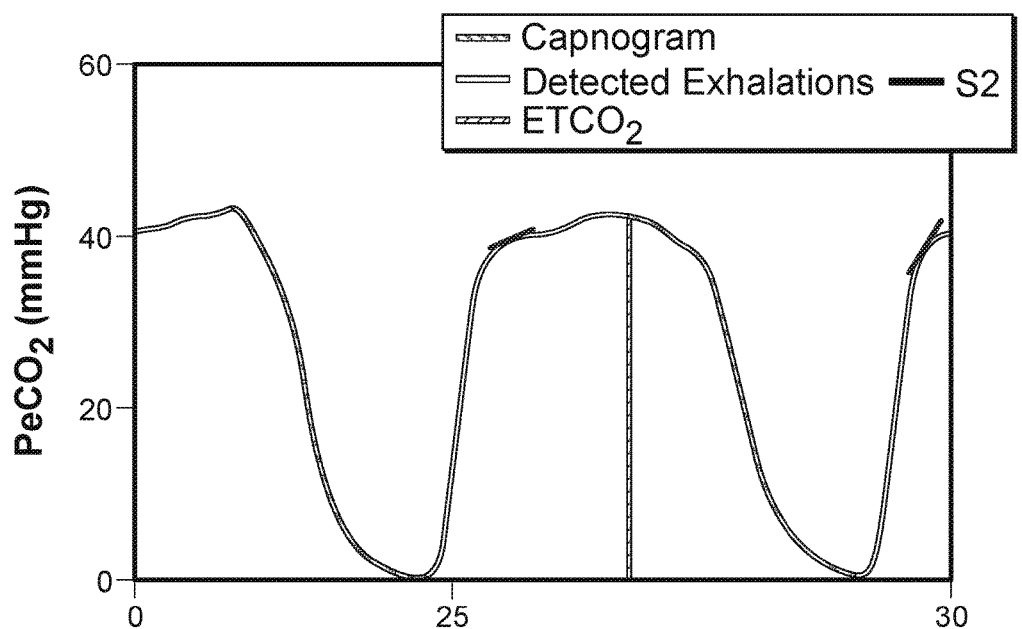
FIG. 7 is a diagram of a capnogram, including a feature of a slope at an intermediate portion of an exhalation, according to an illustrative implementation of the disclosure.

FIG. 7 is a diagram of a capnogram, including a feature of a slope at an intermediate portion of an exhalation, S2. In an example, to extract the intermediate slope S2, the system of the present disclosure implements a linear regression over the middle fifth of exhalation. For example, the slope S2 may be obtained using a least squares fit to capnogram samples in multiple exhalation segments for the patient.

Figure 8:
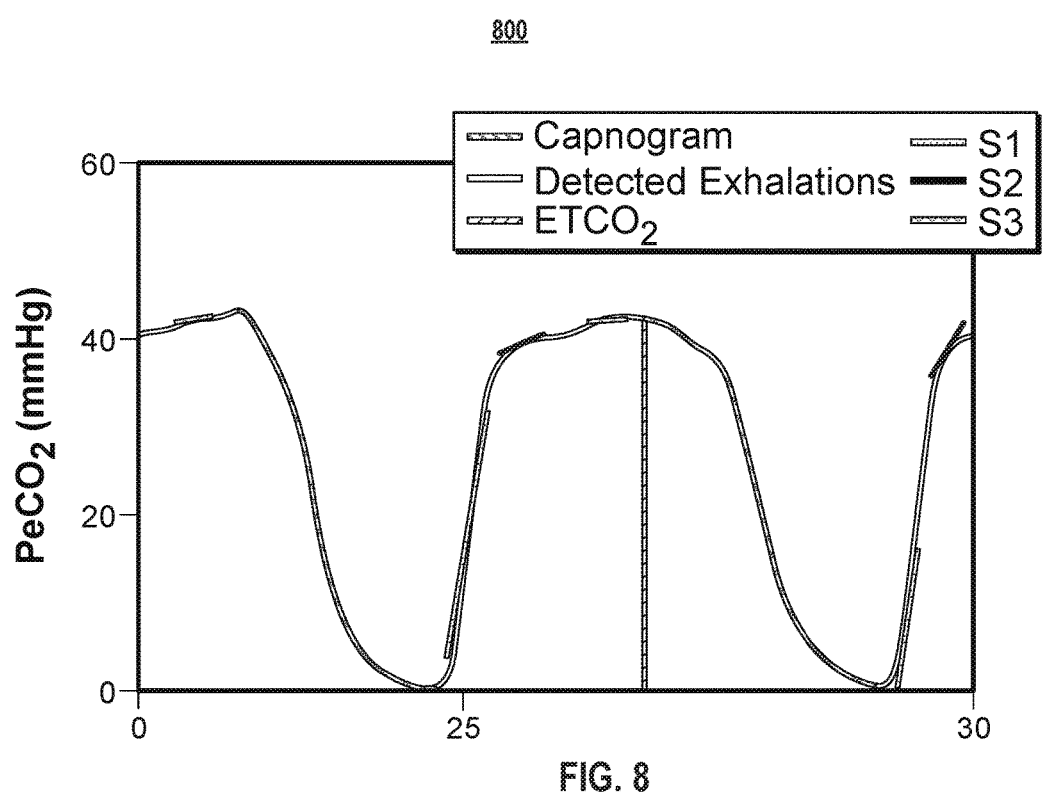
FIG. 8 is a diagram of a capnogram, including a feature of a slope at an initial portion of an exhalation, according to an illustrative implementation of the disclosure.

FIG. 8 is a diagram of a capnogram, including a feature of a slope at an initial portion of an exhalation, S1. In an example, to extract the initial exhalation slope S1, the system of the present disclosure implements a linear regression from the first tenth to the third tenth of exhalation. The slope ratio S2/S1 has been shown to help distinguish capnograms from asthmatics and normal patients.[7] S2/S1 is therefore an important parameter in determining the physiological state of a patient.

[7] See B. You et al. "Expiratory capnography in asthma evaluation of various shape indices," *Eur. Respir. J.*, vol. 7, pp. 318-323, 1994, which is herein incorporated by reference in its entirety.

Figure 9:
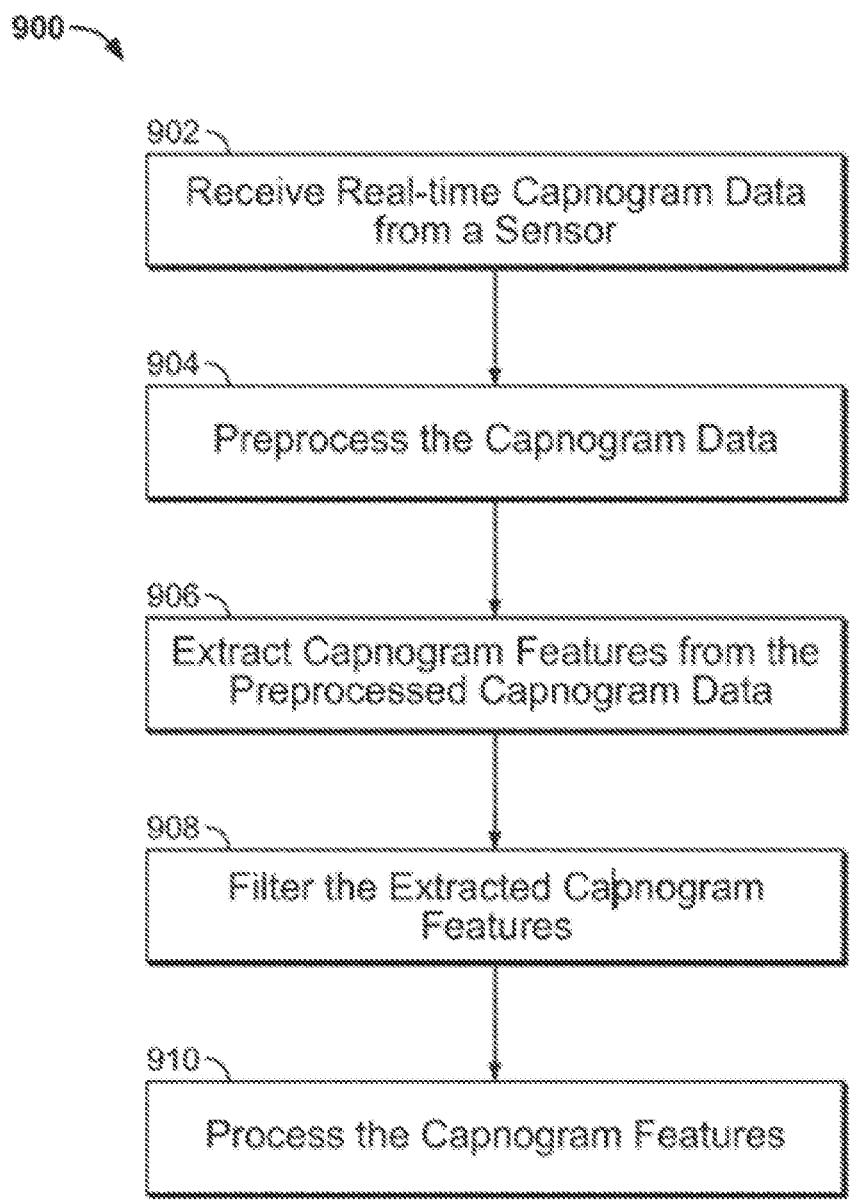
FIG. 9 is a flow diagram depicting a process for processing capnogram features, according to an illustrative implementation of the disclosure.

FIG. 9 is a flow diagram depicting a process 900 for processing capnogram features. At step 902, a processor may receive real time data from a sensor measuring carbon dioxide concentration in a breath receiver in fluid communication with a patient undergoing procedural sedation. At step 904, the processor may preprocess the capnogram data. Capnogram data can be acquired continuously or at prefixed intervals from the time domain. Preprocessing steps, including decimation or low-pass filtering to reduce noise and quantization effects, may be utilized. Time domain analysis of the capnogram may include preprocessing, detection of distinct exhalations by slope changes, determination of exhalation duration, end-exhalation slope, $ETCO_2$, time spent at $ETCO_2$, and curve length. Monitoring time-domain features can be incorporated into the larger system to predict sedation state and respiratory function.

At step 906, the processor may extract capnogram features from the preprocessed capnogram data, including capnogram features such as $ETCO_2$, S1, S2, and S3, as described above. A frequency/spectral domain analysis of the capnogram data may be used, in combination with time domain analysis, to extract capnogram features. Spectral domain components, i.e., frequency domain analysis at prefixed or varying time intervals, may be extracted through at least one of short-time Fourier transforms, wavelet transforms, and power spectral density analyses. Spectral domain components may provide direct measures of localized signal variability and periodicity. The analytical methods may be parameterized by at least one of window size, hop length, and window shape. Extracted features include, but are not limited to, 95% spectral edge frequency or other measures of spectral extent, degree-of-periodicity indices, and discrete wavelet coefficients. Periodicity indices may provide information on the shape and regularity of patient breathing over a fixed duration of time.

At step 908, the processor may filter capnogram features. The breath-by-breath feature time series may be causally median filtered and then standardized (subtracting an approximate mean value and dividing by an approximate standard deviation) for subsequent analysis.

At step 910, the processor may process capnogram features to determine a physiological state of a patient. The process of step 910 is further described in relation to the exemplary embodiment of FIG. 10.

Figure 10:
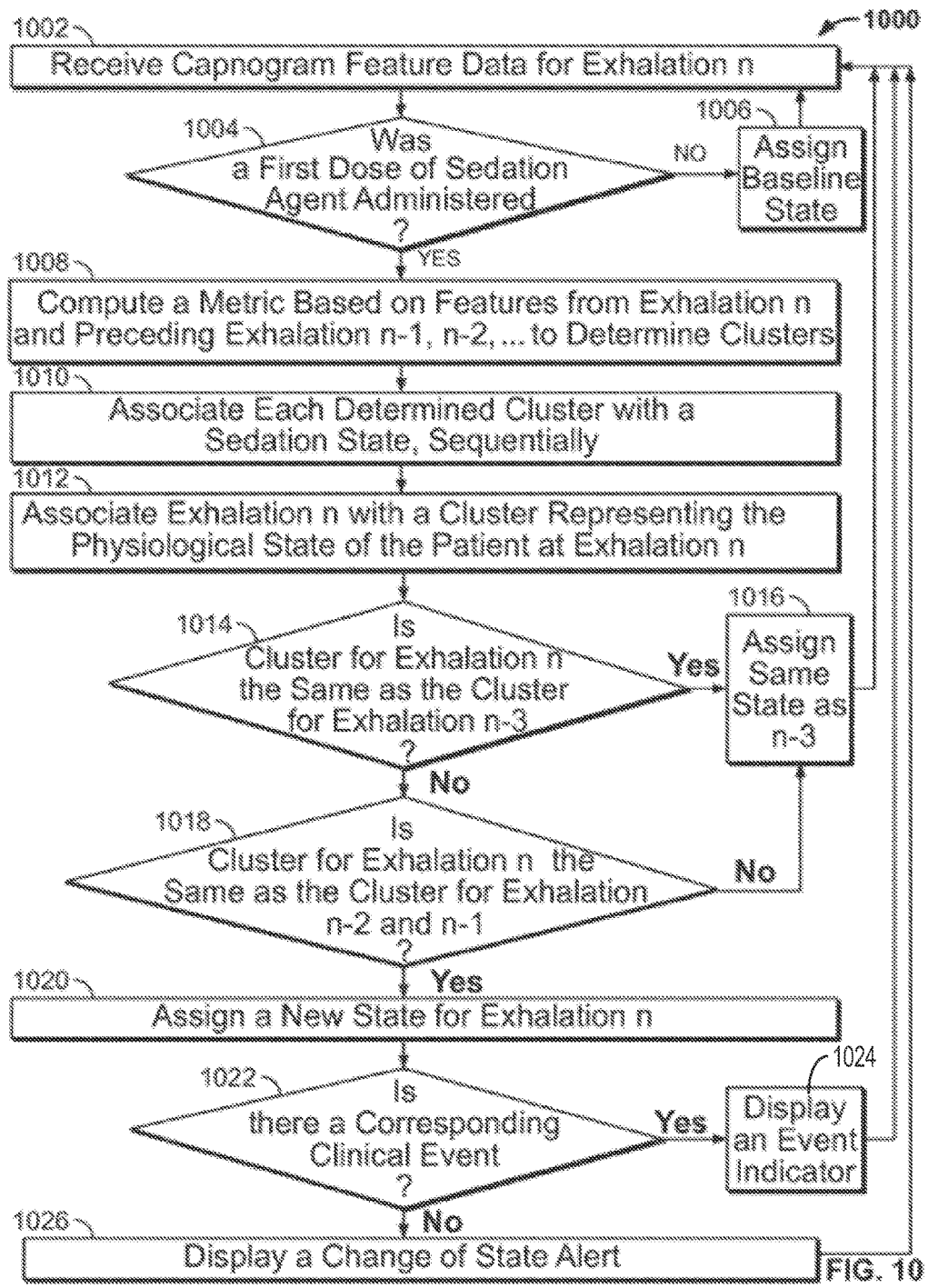
FIG. 10 is a flow diagram depicting a process for determining a physiological state of a patient associated with extracted capnogram features and displaying the results of the determination, according to an illustrative implementation of the disclosure.

FIG. 10 is a flow diagram depicting an exemplary embodiment of a process 1000, corresponding to a causal clustering technique, to determine a physiological state of a patient associated with extracted capnogram features and to display the results of the determination.

At step 1002, the system may receive capnogram feature data for an n-th exhalation. At step 1004, the system may determine whether the first dose of procedural sedation agent has yet been administered for that patient. In the event that the first dose has not yet been administered, the method may proceed to step 1006, where it may assign the current physiological state as the baseline state, before returning to step 1002. In the event that the first dose has been administered, the method may proceed to step 1008.

At step 1008, the method may apply a clustering technique that computes a metric based on features extracted from exhalations n and preceding exhalations (numbered n−1, n−2, etc.), to determine a set of data clusters indicative of possible physiological states of the patient. Each cluster may be represented by its centroid. In the exemplary embodiment of FIG. 10, and throughout this disclosure, the metric may be a multi-parameter metric, as described below. The number of clusters, k, may be specified by the user or determined by the clustering technique. A k-means clustering technique using the Euclidean distance metric may be implemented.[8] The starting or initialization values for computation of the centroids at stage n may be the centroids determined at stage n−1. In this exemplary embodiment, the clustering technique may be a causal clustering technique which uses prior cluster information to guide the present clustering. The determination of the number of clusters k may be accomplished by requiring the intra-cluster separation of features to be small relative to the inter-cluster separation. At step 1010, the method may label or number the clusters, associating each determined cluster with a sedation state, sequentially. For example, the cluster associated with exhalations that preceded the first dose of procedural sedation agent may be labeled as the baseline state or "sedation state 0", and the clusters encountered sequentially in subsequent exhalations up to exhalation n may be numbered as sedation states 1 through k−1. In procedural sedation, k may be in the range of two to ten, depending on the patient or procedure, analogous to the qualitative rating of various subjective clinical sedation scales, such as the Ramsay Sedation Scale. For example, the Ramsay scale indicates that a patient at level 1 is anxious, agitated, restless; a patient at level 2 is cooperative, oriented, tranquil; a patient at level 3 responds only to verbal commands; a patient at level 4 is asleep, with a brisk response to light stimulation; a patient at level 5 is asleep, with a sluggish response to stimulation; and a patient at level 6 is unarousable. Alternatively, other scales such as the Richmond Agitation and Sedation Score (RASS) or the Riker Sedation-Agitation Scale (SAS) provide scores from −5 to +4, and from 1 to 7, respectively, both going from dangerous agitation to unarousable. At step 1012, the method may use the computed

[8] See J. B. MacQueen, "Some methods for classification and analysis of multivariate observations," *Proc. 5$^{th}$ Berkeley Symp. Math. Stat. Prob.*, pp 281-297, 1967, which is herein incorporated by reference in its entirety. metric to associate exhalation n with one of the clusters in the cluster set which best represents the physiological state associated with exhalation n, based on the features of exhalation n. The method may further compute a measure of confidence in the assignment of exhalation n to a particular cluster, based on the relative distances of the features of this exhalation from the various clusters, as determined by the metric.

In an embodiment, an unsupervised learning technique other than a k-means clustering technique may be used. For example, mixture models or hierarchical clustering may be used. Alternatively, expectation-maximization techniques, principal component analysis, independent component analysis, singular value decomposition or any other causal technique may be used.

In an embodiment, a semi-supervised or supervised learning technique may be used, with a physician providing input on part of the data, e.g., labeling certain features or data from a patient. Machine learning may take place with data collected on a single patient undergoing a single procedure, but machine learning may also take place with data collected on a single patient over multiple procedures, or multiple patients undergoing a variety of procedures. A training stage, testing stage and application stage may be used for the machine learning, similar, for example, to the training, testing and application stages described in FIGS. 2-5 of U.S. application Ser. No. 13/849,284 for example.

Returning to step 1008, in an exemplary embodiment, a set of three (i.e., k=3) clusters and associated centroids may be found at stage n, using information from the current and past exhalations. Centroid separation metrics for use in evaluation of the quality of clustering or choice of k may include centroid triangle area in the case where k=3 (or the analogous centroid simplex volume for k>3) and average intercentroid distance. The centroid triangle area is hereby defined as the area of the triangle with vertices located at the three centroids in the plane defined by those centroids. Average intercentroid distance is hereby defined as the average Euclidean distance between each pair of centroids. In this exemplary embodiment where k=3, at step 1010, the three clusters may be labeled as the "baseline state," "sedation state 1" and "sedation state 2," sequentially. In this exemplary embodiment, at step 1012, the current exhalation is assigned to a cluster. The assignment to a cluster may take into account, in addition to the value of the metric, information input from other patients, procedures, or physicians in the case of a semi-supervised or supervised learning technique. For example, additional data taken into account for clustering may include patient demographic and physiological data or indicators (e.g., age, weight, allergies, conditions) or a pharmacokinetic model and/or a pharmacodynamic model of drugs and procedural sedation agents, providing information on how the sedation agents or drugs propagate and affect sedation for a particular patient or patients in general.

As shown in steps 1014-1020, in this exemplary embodiment a state change, i.e., a change in the state of sedation of the patient may be confirmed after three consecutive exhalations are assigned to the same new cluster, i.e., after the patient has been in a new state of sedation for at least three exhalations. At step 1014, the method may determine whether the cluster selected for exhalation n is the same as the cluster for exhalation n−3. In the event that the cluster for exhalation n is the same as the cluster of exhalation n−3, the method proceeds to step 1016, where the physiological state assigned to exhalation n is the same as the physiological state assigned to exhalation n−3, and the method returns to step 1002 to repeat process 1000 for the next exhalation. In the event that at step 1014 the cluster for exhalation n and the physiological state corresponding to exhalation n is different from the cluster and corresponding physiological state for exhalation n−3, the method proceeds to step 1018 to check whether the cluster for exhalation n is also different from the cluster for exhalation n−2 and exhalation n−1. If the cluster for exhalation n is not the same as the cluster for exhalation n−2 or exhalation n−1, there is no change in physiological state, and the method returns to step 1016 and step 1002. Alternatively, if the cluster for exhalation n is the same as the cluster for exhalation n−2 and exhalation n−1, the method proceeds to step 1020, where a new sedation state may be assigned. The resulting physiological state may be labeled according to when it occurs during the procedural sedation. For example, the patient's state before the first drug administration is labeled as "Baseline." Subsequent states may be labeled "Sedation1" and "Sedation2" in sequential order, for example. The clustering technique assigns each exhalation into a cluster corresponding to a sedation state and corresponding patient sedation level. As noted above, assignment to a cluster may be based on the value of the metric and additional information such as demographic and physiological data about the patent undergoing procedural sedation, or information from other patients and other procedures. Because sedation is a continuum, assigning a distinct state to each moment during sedation may be difficult. However, exemplary definitions for mild sedation, moderate sedation and deep sedation are provided below.

Mild sedation may be a drug-induced state during which patients respond normally to verbal commands. Although cognitive function and coordination may be impaired, ventilatory and cardiovascular functions are unaffected. Moderate sedation may be a drug-induced depression of awareness during which patients respond purposefully to verbal commands, either alone or accompanied by light tactile stimulation. No interventions are required to maintain a patent airway, and spontaneous ventilation is adequate. Deep sedation may be a drug-induced depression of awareness during which patients cannot be easily aroused but respond purposefully following repeated or painful stimulation. The ability to independently maintain ventilatory function may be impaired. Patients may require assistance in maintaining a patent airway, and spontaneous ventilation may be inadequate.

The method described in relation to the exemplary embodiment of FIG. 10 may also use additional data to further discern the physiological meaning of the clusters and attach more definitive labels such as "mild sedation" or "deep sedation." For example, the method may determine whether there are clinical events within a certain time of exhalation n. Clinical events may include drug administration, the start and end of the medical procedure, or other clinical interventions such as airway repositioning, verbal or tactile stimulation, and administration of supplemental oxygen. The method may also use data associated with standard monitoring methods, including pulse oximetry, automated blood pressure measurement, respiratory rate, and visual assessment. One or more additional inputs may be EEG, auditory evoked potentials, galvanic skin (or electrodermal) response, pulse oximetry monitoring, breath gas monitoring, and electrocardiogram (ECG) monitoring. The method may incorporate other information such as patient data, medication type and dosage, physiological data (respiratory rate, oxygen saturation, heart rate, electrodermal response), procedural data, outputs from a pharmacokinetic, pharmacodynamic, or ventilatory model, or video recording. Demographic or clinical parameters obtained from procedural documentation may include age, weight, gender, procedure type, and medication data. Sedation scoring systems such as the Ramsay Sedation Scale, Sedation Agitation Scale, and Motor Activity Assessment Scale, among others, may be used in combination with the metric to correlate capnogram data with physiological states. In addition, physiological and/or procedural data may be used to assess a relative predictive value of signal monitoring. Monitoring of patients is described, for example, in U.S. Pat. No. 7,031,857 by Tarassenko, and U.S. Pat. No. 8,414,488 by Colman, both of which are incorporated herein by reference in their entirety.

Referring back to FIG. 10, at step 1022, the method may determine whether there is a clinical event corresponding to the new state. In the event that a clinical event corresponds to the new state, the method proceeds to step 1024 where it may display an indicator of a change in state. Alternatively, if there is no corresponding clinical event associated with the change in state, the method proceeds to step 1026 where it may display an alert to a physician. Alternatively if no change in physiological state is detected and no clinical event is detected, the method and system described herein may continue to display real-time information, including for example the traces shown in FIG. 11 and described below.

Steps 1024 and 1026 may be carried out by a clinical monitoring system connected to a breath receiver and to other sensors and/or sources of data, and may display real-time indicators relating to respiratory function, sedation level, and drug titration. The clinical monitoring system may be a standalone monitor, or a component of a monitoring system, for example, a monitoring system used in emergency departments, procedural sedation services, or gastroenterology, dental, and other specialty offices. The clinical monitoring system may perform real-time signal processing and analysis to implement both monitoring and predictive functionalities in procedural sedation. The clinical monitoring system may also make recommendations for clinical interventions, including, but not limited to, nature, amount and timing and frequency of drug administrations, airway maneuvers, or the need for additional oxygen. For example, when the system detects a change in a sedation level of the patient during a procedure, the system may alert the physician with a sound alarm, along with a visual indicator. The alert may also be accompanied by a recommendation for an action, and/or may be accompanied by an indication of the next step for the system. For example, the alert may display "Patient Awakening" and "Inject Additional Dosage." A physician may then let the system proceed, and/or override or supplement the actions automatically suggested by the system.

Process 1000 may use an inference system utilizing support vector machines, and/or machine learning techniques, and/or statistical inference to determine and predict sedation states. Training and analysis may employ subsections or complete sets of parameter data values. Empirical approaches such as clustering, hidden Markov models, and neural network models may be used to train the processor performing process 1000 to establish connections between various physiological parameters and sedation states. For example, the system may learn to detect certain drug administrations greater than certain threshold dosage. Alternatively, the system may learn to correlate certain risk factors (e.g., high blood pressure, or a history of asthma) with specific capnogram indicators. As noted above, the technique implemented on the system may learn during the course of a procedure for a single patient. Alternatively, the technique implemented on the system may also learn and evolve by acquiring information from multiple patients over multiple procedures. In an additional embodiment, the system may provide recommendations or comments based on the machine learning process. For example, the system may display a message "60% of patients with congestive heart failure experience apnea after the second drug administration. Do you want to continue?" In another example, the system may display a message such as "Reminder: 90% of children needed an additional drug dose after the start of the procedure." Non-capnographic predictive systems are described, for example, in U.S. Pat. No. 7,398,115 by Lynn, which is incorporated herein by reference in its entirety.

It is noted that all steps of method 1000 may be performed in real time, where "real time" is defined herein as being any time scale giving the health care provider sufficient time to respond to a medical situation. "Real time" may be, for example, in the range of seconds (for example, 0 to 120 seconds), in the range of minutes (for example, 1 to 10 minutes), and the like.

Figure 11:
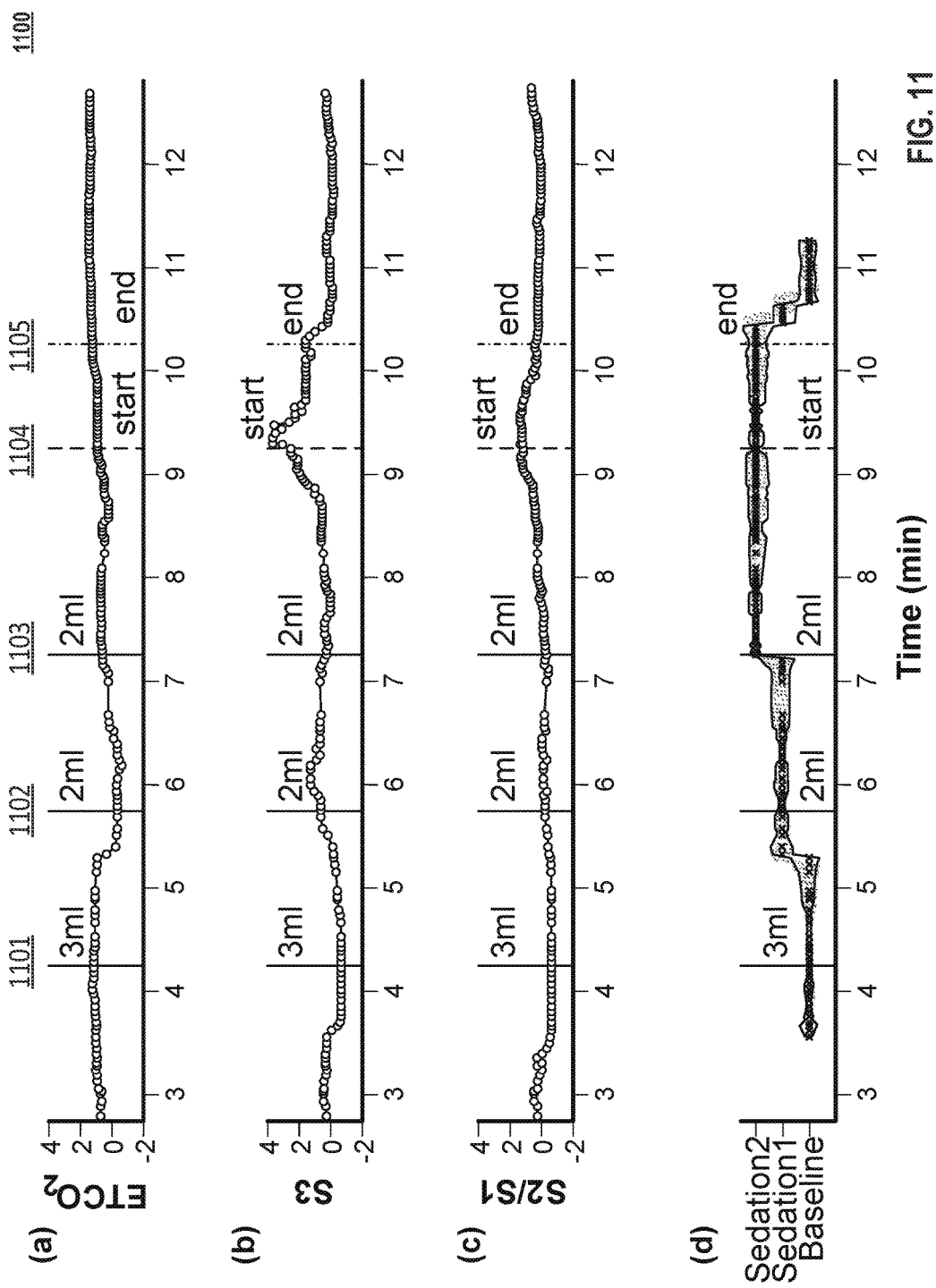
FIGS. 11-14 depict the time evolution of features from capnograms of patients undergoing procedures, and the corresponding time evolution of the sedation state of the patients, with associated confidence bands, according to illustrative implementations of the disclosure.

FIG. 11 includes graphs depicting the time evolution of features from capnograms of patients undergoing procedures, and the corresponding time evolution of the sedation state of the patients, with associated confidence bands, according to illustrative implementations of the disclosure. The graphs are of an exemplary embodiment, depicting key features extracted after processing from a capnogram of a 75-year-old female patient, according to an illustrative implementation of the disclosure. Data shown in the graphs excludes pre- and post-procedure movements and artifacts (such as patient verbalization or movement) and may only consider data from one minute before a first event (e.g., first drug administration) and until one minute after the last procedure event. The first (i.e. top) graph depicts, on the y-axis, $ETCO_2$ as a function of time. The second graph depicts, on the y-axis, end exhalation slope S3 as a function of time. The third graph depicts, on the y-axis, a ratio S2/S1 of a slope at an intermediate portion of exhalation (S2) over a slope at an initial portion of exhalation (S1). Critical phases of procedural sedation indicated on the graphs, as marked by clinical staff, comprise initial drug administration, titration to maintain level and duration of sedation appropriate to the procedure, and return to baseline. Markers 1101-1105 indicate some of these events. Markers 1101, 1102, and 1103 indicate administration of a drug (e.g., propofol), and marker 1104 indicates the start of a procedure (in this case, cardioversion), and marker 1105 indicates the end of the procedure. Even to an informed observer such as a medical professional, there may not be a clearly identifiable correlation between the critical phases of procedural sedation marked by clinical staff and the parameters extracted from the capnogram, shown in FIG. 11.

The last (i.e., bottom) graph in FIG. 11 is a diagram depicting the evolution of the sedation state of the same patient, based on features extracted from the capnogram, according to an illustrative implementation of the disclosure. The change in sedation state is represented by plotting the sedation metric described in relation to FIG. 10 graphically over time, with the same markers 1101, 1102, 1103 as in the first three graphs indicating drug administration, and markers 1104 and 1105 indicating the start and end of the actual procedure (cardioversion in this case). For example, the last graph shows causal clustering of the multi-parameter metric computed from $ETCO_2$, S3, and S2/S1, with the state before drug administration labeled "Baseline," the next sedation state labeled "Sedation1," and the third sedation state labeled "Sedation2." In contrast to the first three graphs, which may be difficult to read and provide little to no insight on sedation level, the last graph shows patient-specific clustering results which reflect physiologic changes in patient state over the course of procedural sedation. Use of the multi-parameter metric enables the extraction of additional quantitative information from the capnogram that serves to define distinct patient states that correlate with sedation events. For example, while no clear delineation between states may be observed based on the $ETCO_2$, S3, or S2/S1 parameters individually or collectively in the first three graphs, the metric shown in the last graph indicates three distinct sedation levels, which coincide in time with clinical events corresponding to markers 1101-1105, and are strongly correlated with these clinical events, the last graph clearly shows the progression of the physiological state of the patient from baseline through a light sedation state ("Sedation1") to a final sedation state ("Sedation2") as additional boluses of sedation agent are administered, and then the recovery through light sedation and then to baseline at the end of the procedure, as the sedation wears off. Furthermore, the degree of uncertainty in the assignment of patient sedation state is indicated in this embodiment by the grey area on either side of the dark trace that represents sedation state. A wider grey area or band indicates a greater degree of uncertainty, or equivalently a lower degree of confidence, in the assignment. It will be noted that wider uncertainty bands typically precede the transition from one sedation state to the next, indicating that the preceding sedation label is becoming increasingly untenable in the face of the data that is being currently processed.

Figure 12:
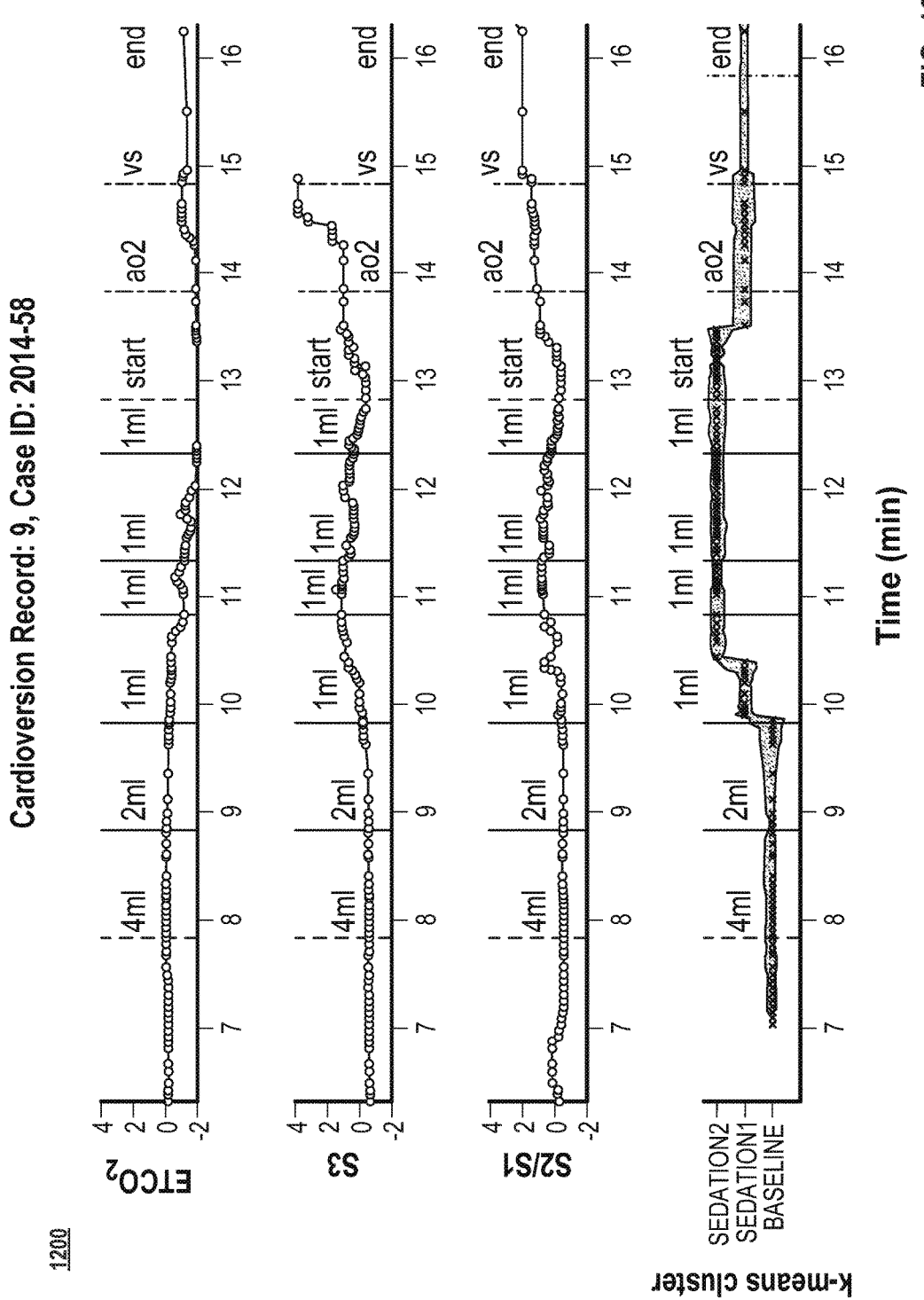

FIG. 12 is an example of a diagram depicting the time evolution of features extracted from a capnogram, as for the first three graphs of FIG. 11, after processing, and the corresponding time evolution of the sedation state of the patient, as for the final graph of FIG. 11, after causal clustering using a multi-parameter metric based on those features, according to an illustrative implementation of the disclosure, for a patient undergoing a procedure. Various associated events (administrations of sedation agents, start and end of procedure, adverse events, interventions) are also marked. In the exemplary embodiment of FIG. 12, the patient displayed multiple intervals of apnea "ap", as evidenced by $ETCO_2$ falling to its lowest value or being undetectable, then received supplemental oxygen "o2" at time t=14 minutes, and verbal stimulation "vs" at time t=15 minutes. As indicated by the evolution of the sedation state, represented by the metric plotted in the bottom trace, these interventions occurred as the patient moved to a lighter sedation state, "Sedation1".

Figure 13:
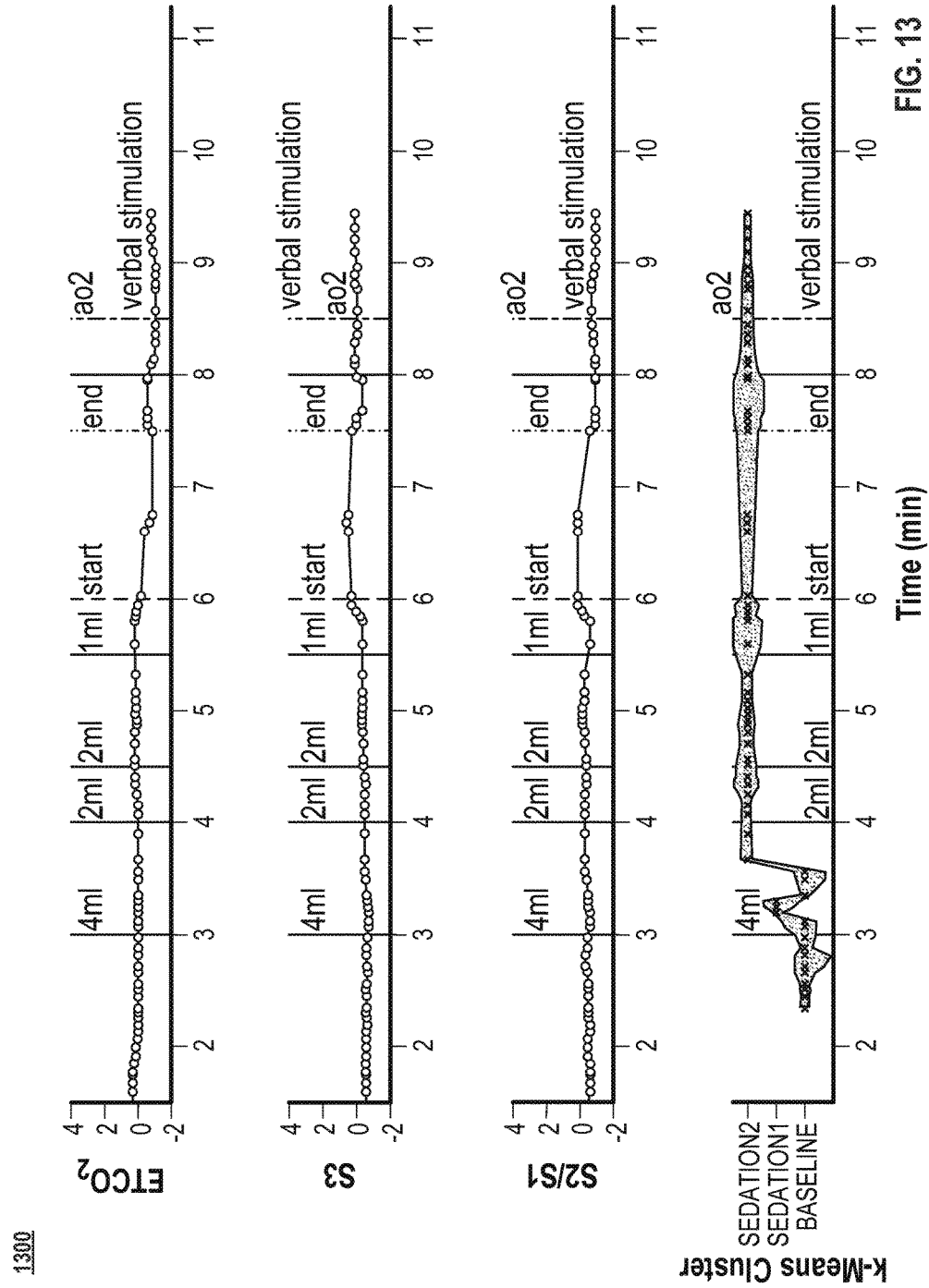

FIG. 13 is an example of diagrams depicting the time evolution of features extracted from a capnogram, as for the first three graphs of FIG. 11 after processing, and the corresponding time evolution of the sedation state of the patient, as for the bottom graph of FIG. 11, after causal clustering using a multi-parameter metric based on those extracted features, according to an illustrative implementation of the disclosure, for a patient undergoing a procedure. As in FIG. 12, various associated events are also marked. In the exemplary embodiment of FIG. 13, the patient received verbal stimulation and additional oxygen simultaneously at time t=8.5 minutes. The sedation state plotted in the bottom trace remained at "Sedation2" during this interval, indicating that this combined stimulation and oxygen was insufficient to bring the patient out of the heavier sedation state during the period of monitoring.

Figure 14:
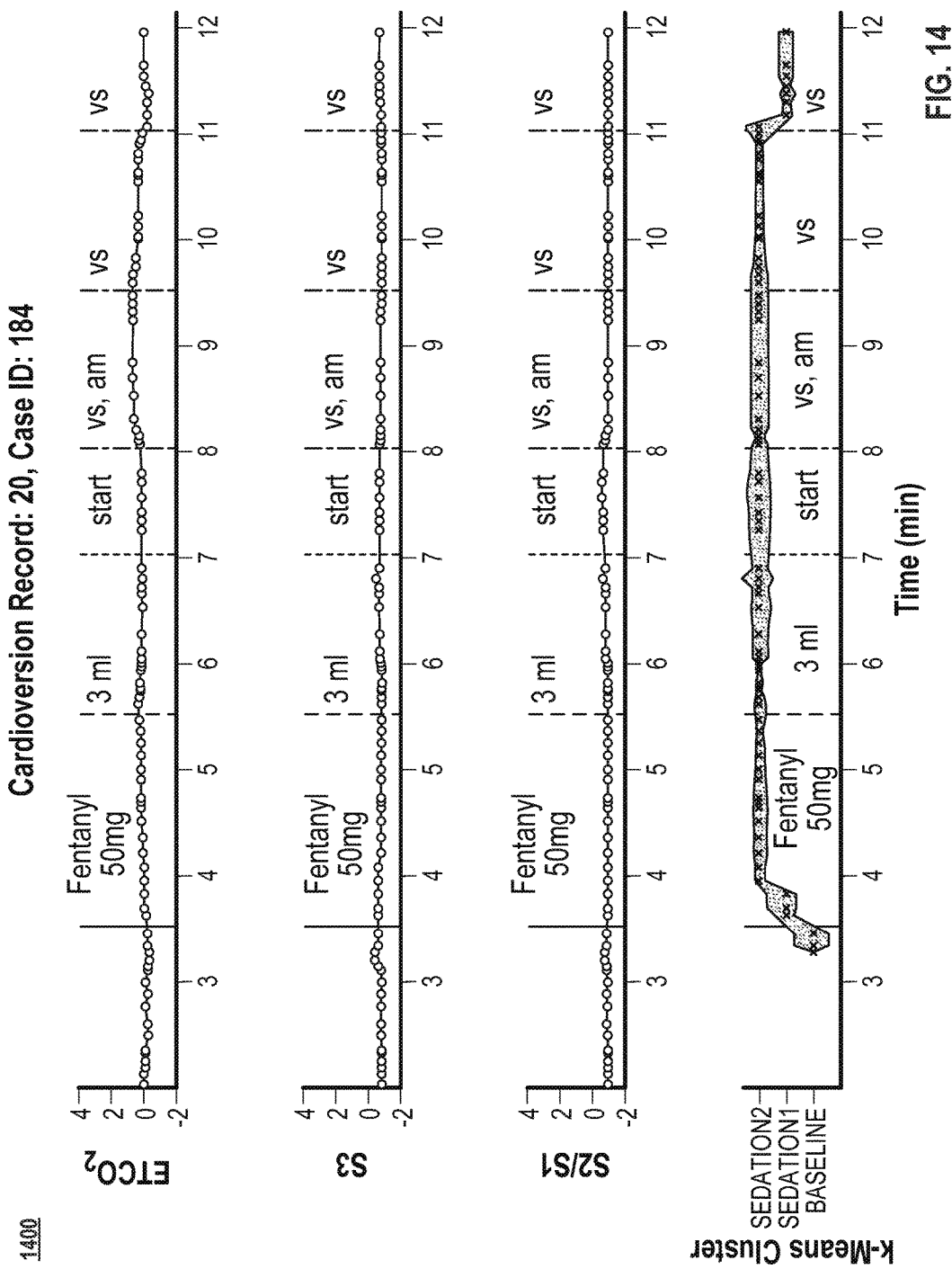

FIG. 14 is another example of diagrams depicting the time evolution of features extracted from a capnogram, as in the first three graphs of FIG. 11, after processing, and the corresponding time evolution of the sedation state of the patient, as in the last graph of FIG. 11, after causal clustering using a multi-parameter metric based on those features, according to an illustrative implementation of the disclosure, for a patient undergoing a procedure. As in FIG. 12, various associated events are also marked. In the exemplary embodiment of FIG. 14, the patient received repeated verbal stimulation indicated by vertical bars and the label "vs", and also received an airway maneuver, performed at time t=8 minutes. The evolution of the sedation state, represented by the plotted metric in the bottom trace, indicates that the patient experienced no change in level of sedation despite the initial verbal stimulation and the airway maneuver, but that a change to a lighter sedation level "Sedation1" was observed after the third verbal stimulation at time t=11 minutes.

Figure 15:
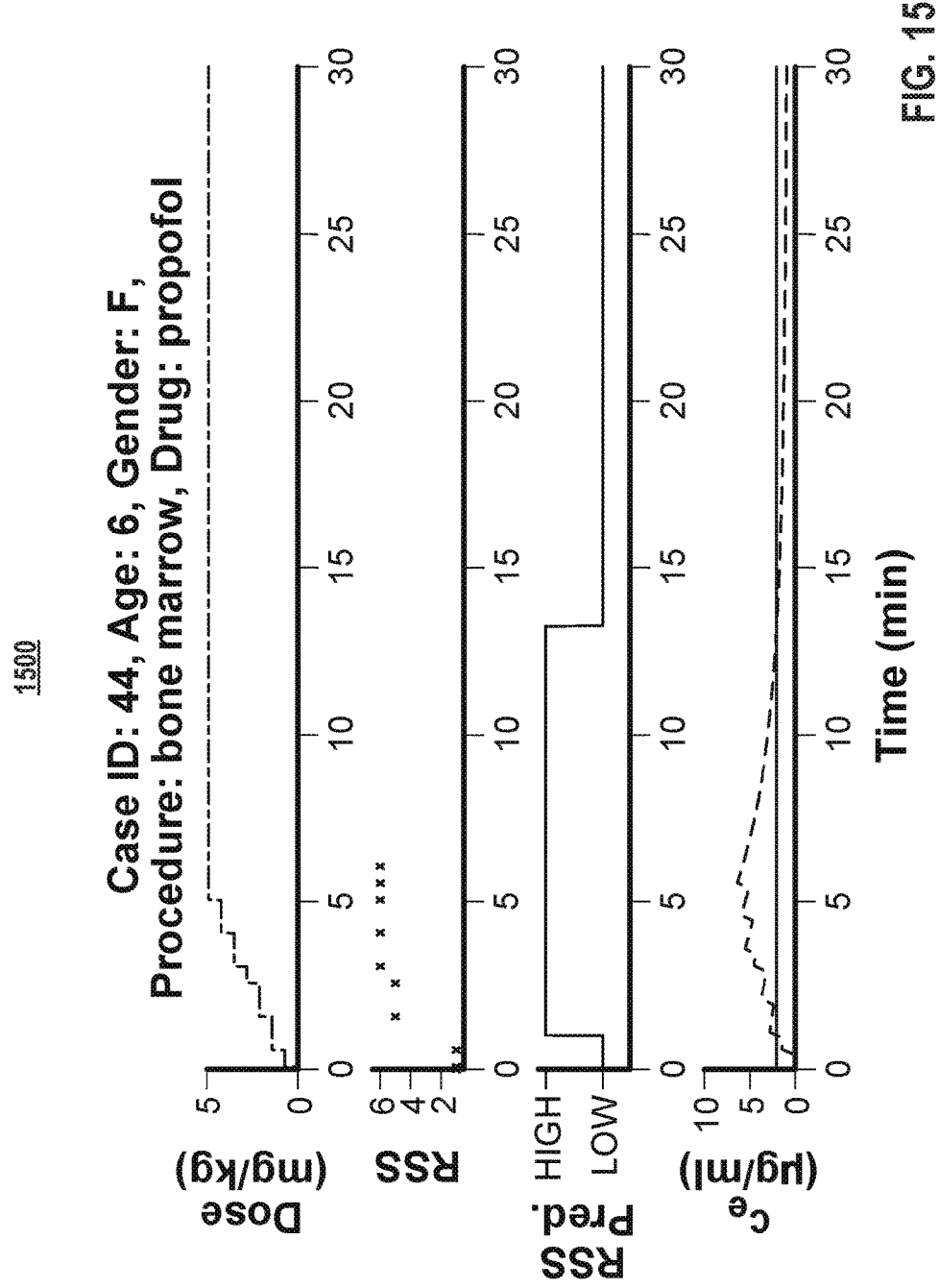
FIG. 15 displays the cumulative administered dose (top panel), the recorded Ramsay Sedation Score (RSS, second panel), the predicted RSS (third panel) based on thresholding the continuously estimated effect-site concentration (fourth panel), for a single patient undergoing procedural sedation with propofol, according to an illustrative implementation of the disclosure.

FIG. 15 displays the cumulative administered dose (top panel), the recorded Ramsay Sedation Score (RSS, second panel), the predicted RSS (third panel) based on thresholding the continuously estimated effect-site concentration (fourth panel), for a single patient undergoing procedural sedation with propofol, according to an illustrative implementation of the disclosure. The estimated effect-site concentration is shown in micrograms per milliliter on the y-axis, and time is shown on the x-axis, which is the same for all plots in FIG. 15. The first (i.e. top) plot shows the cumulative dose of propofol administered over time. The second plot indicates the Ramsay Sedation Score, shown on the y-axis, which was annotated at several points, represented by x marks, during the procedure. The estimated effect-site concentration was used to predict whether the Ramsay Sedation Score equaled or exceeded a threshold of 4, and this prediction is shown in the third plot, which indicates Ramsay Sedation Scores equaling or exceeding the threshold of 4 as 'High' on the y-axis.

Figure 16:
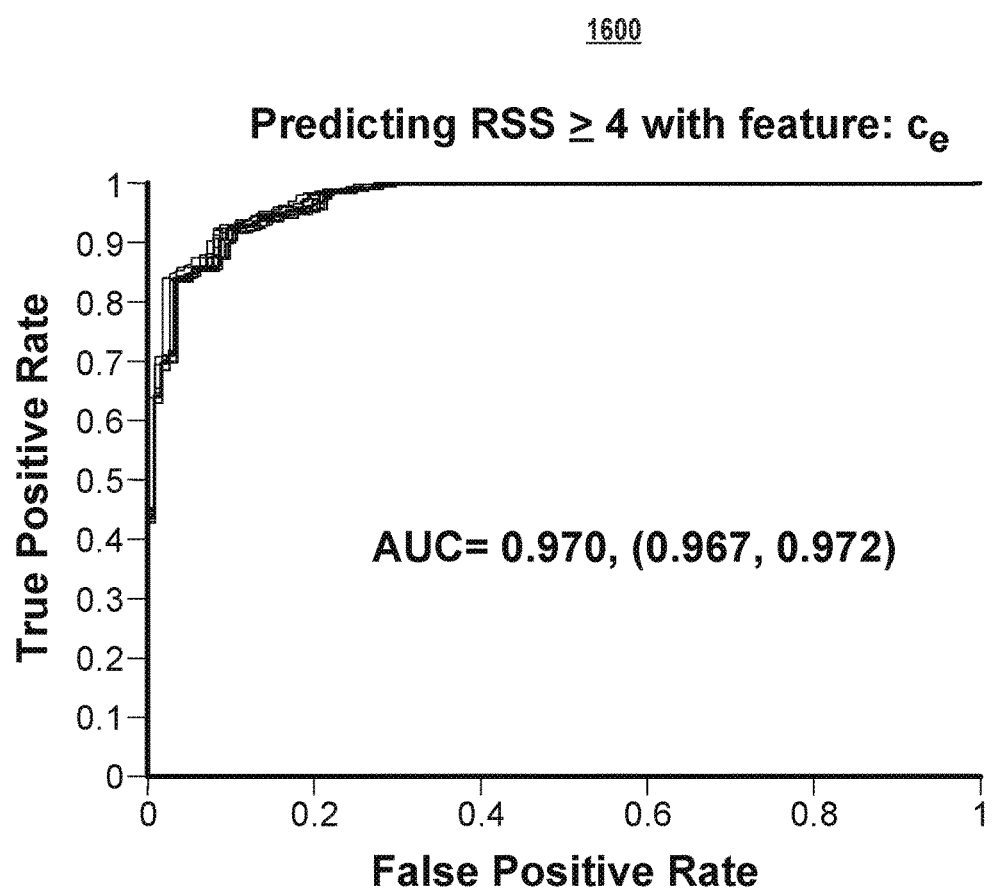
FIG. 16 presents the results from thresholding of the estimated effect-site concentration to predict whether Ramsay Sedation Score equals or exceeds 4 at various points throughout the painful procedures of 38 patients administered propofol for procedural sedation, according to an illustrative implementation of the disclosure.

FIG. 16 presents the results from thresholding of the estimated effect-site concentration to predict whether Ramsay Sedation Score equals or exceeds 4 at various points throughout the painful procedures of 38 patients administered propofol for procedural sedation, according to an illustrative implementation of the disclosure. The x-axis shows the false positive rate, and the y-axis shows the true positive rate. The area under the curve (AUC) for this prediction task is 0.97 with an accuracy of 90.5% at the equal sensitivity/specificity (or "equal error rate") operating point.

Figure 17:
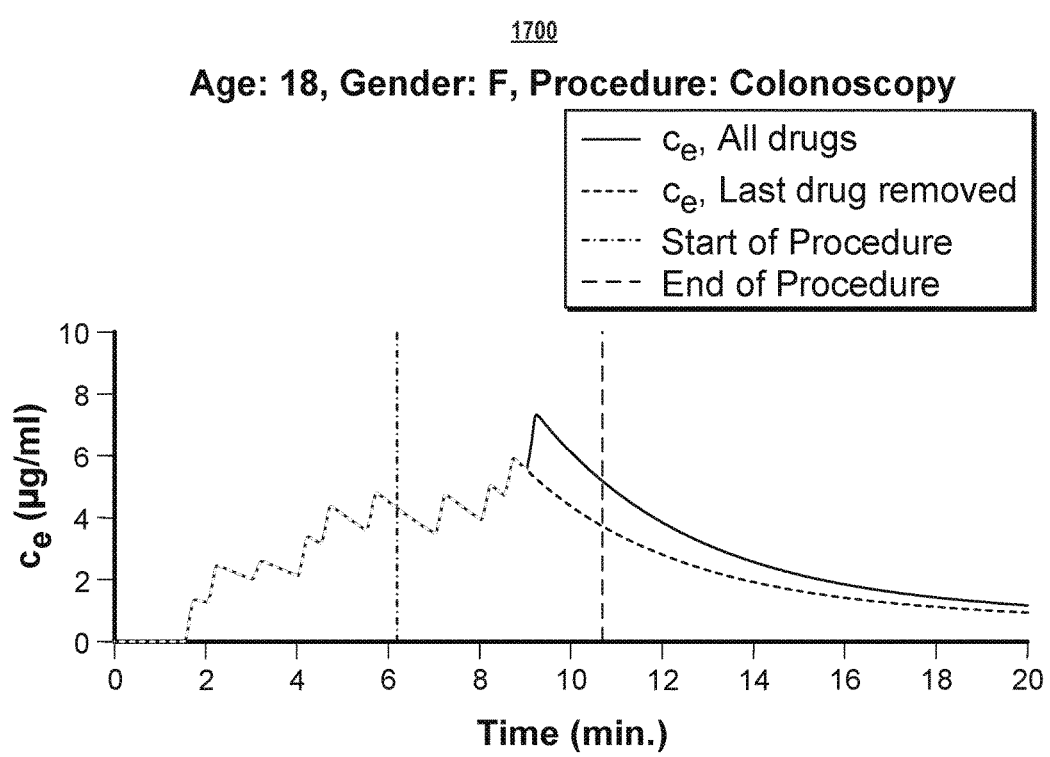
FIG. 17 shows an example from a single patient of the effect-site concentration trajectory with all the administered drug boluses, estimated using a pharmacokinetic model, and also estimated from this model with the last bolus removed; the mean of these two concentrations at the end-time of the procedure is the estimated titration threshold for this case, according to an illustrative implementation of the disclosure.

FIG. 17 shows an example from a single patient of the effect-site concentration trajectory with all the administered drug boluses, estimated using a pharmacokinetic model, and also estimated from this model with the last bolus removed; the mean of these two concentrations at the end-time of the procedure is the estimated titration threshold for this case, according to an illustrative implementation of the disclosure. The y-axis shows the estimated effect-site concentration, and the x-axis shows time. The vertical markers indicate the start time and end time of the painful procedure. The start and end of the procedure were marked by the clinical staff who collected the data. The average of the "all drugs" value and the "last drug removed" value at the time of the end of the procedure constitutes, in this illustrative embodiment, an estimate of the titration threshold that the clinician aims to remain above between the start and end of the procedure.

Figure 18:
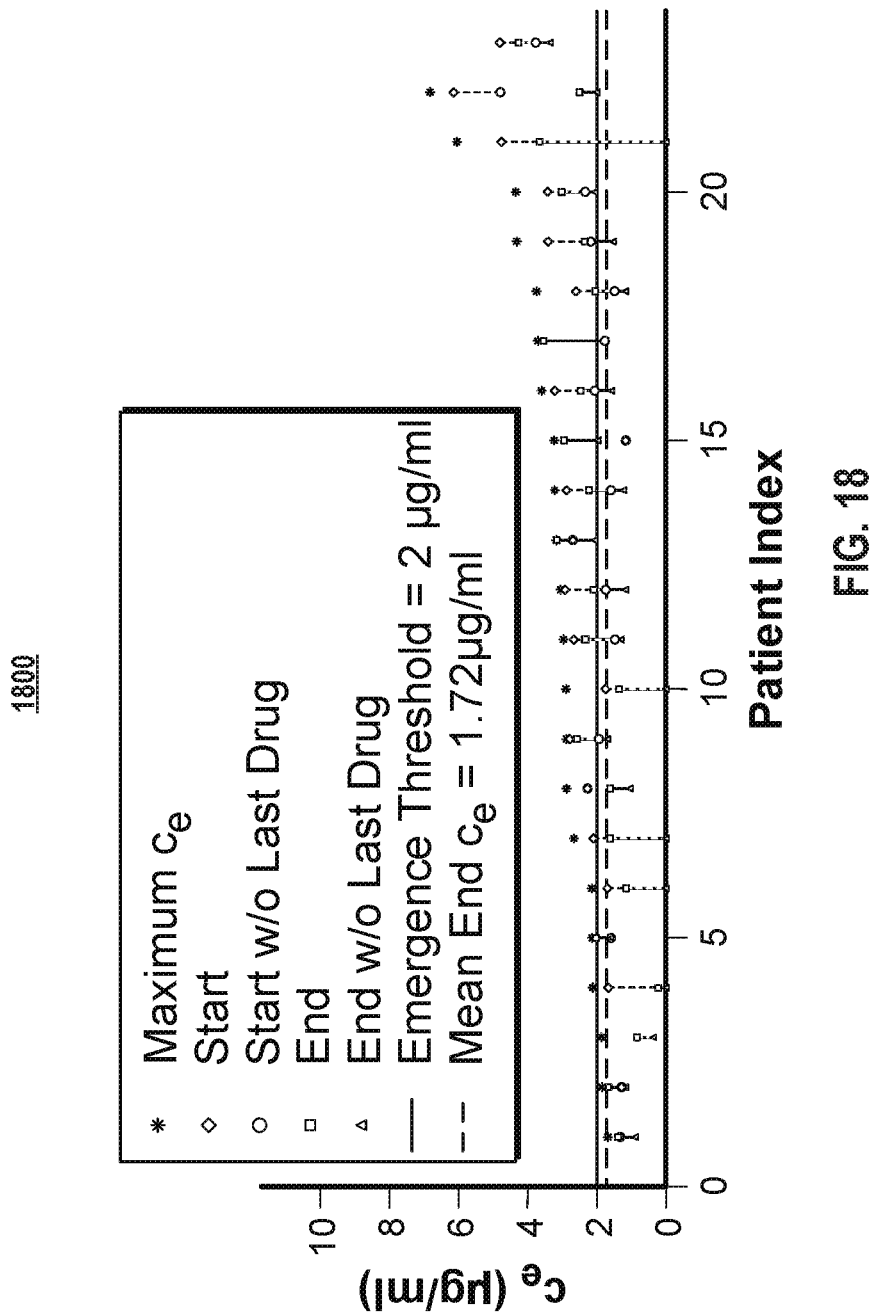
FIG. 18 displays the mean (1.72 micrograms/milliliter) of the estimated titration thresholds for 23 patients receiving propofol during procedural sedation, according to an illustrative implementation of the disclosure.

FIG. 18 displays the mean (1.72 micrograms/milliliter) of the estimated titration thresholds for 23 patients receiving propofol during procedural sedation, according to an illustrative implementation of the disclosure. The titration threshold for each patient was established as described in connection with FIG. 17, namely: the start and end of the procedure were marked by the clinical staff who collected the data; the end-procedure effect-site concentration, shown on the y-axis, of each patient was estimated with all drug administrations, and again without the final bolus administration; and the average of these two values was taken as the estimated titration threshold for that patient. The mean of all these individually estimated titration thresholds constitutes, in this illustrative embodiment, the overall estimated titration threshold for the data set, and aligns well with the drug emergence threshold presented in literature. In another embodiment, as in the simplified model presented in FIG. 19 or using more complicated pharmacokinetic and pharmacodynamics models, plasma concentration rather than effect site concentration may be used to estimate a titration threshold. The titration threshold is estimated at the time the procedure ends since the proceduralist deems it necessary to administer a final bolus in order to render the patient's sedation level sufficient to endure the procedure.

Figure 19:
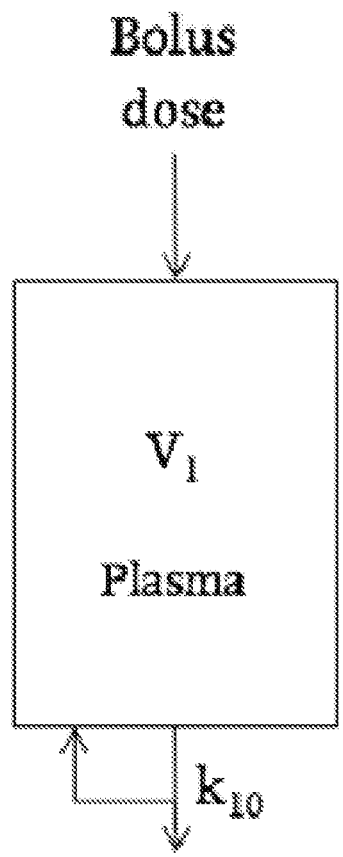
FIG. 19 represents a simplified, single-compartment model to describe plasma concentration during procedural sedation, according to an illustrative implementation of the disclosure.

FIG. 19 shows a simplified single-compartment model to estimate plasma concentration of sedation agent following an input of sedation agent administration amounts and times, according to an illustrative implementation of the disclosure. In the embodiment shown, the sedation agent is administered in discrete boluses. The differential equation used to solve for the plasma concentration as a function of time is shown below the model. The equation relates the rate of change in plasma concentration to plasma concentration $c_p(t)$, bolus administration input dosing information as a function of time u(t), effective or estimated plasma volume $V_1$, and a rate constant $k_{10}$, describing clearance of the sedation agent from the plasma in the following manner: $\dot{c}_p(t) = -k_{10} * c_p(t) + 1/V_1 * u(t)$. The parameters such as plasma volume and $k_{10}$ may be age and gender specific. Bolus doses are administered at times and in doses reflected by the bolus administration input. The cumulative administered dose as a function of time may be a step function of mg/kg of drug administered, or any suitable input function, including possibly a continuous function of time. The plasma volume represents the estimated plasma volume of the patient. The elimination constant reflects the rate at which the drug is expected to be eliminated from the compartment, namely the plasma in this simplified the model. Nominal values of the parameter $V_1$, which is plasma volume, are tabulated for different weights and age groups. The parameter $k_{10}$, which represents elimination rate of the drug from plasma, is known in the literature from experiments.

Figure 20:
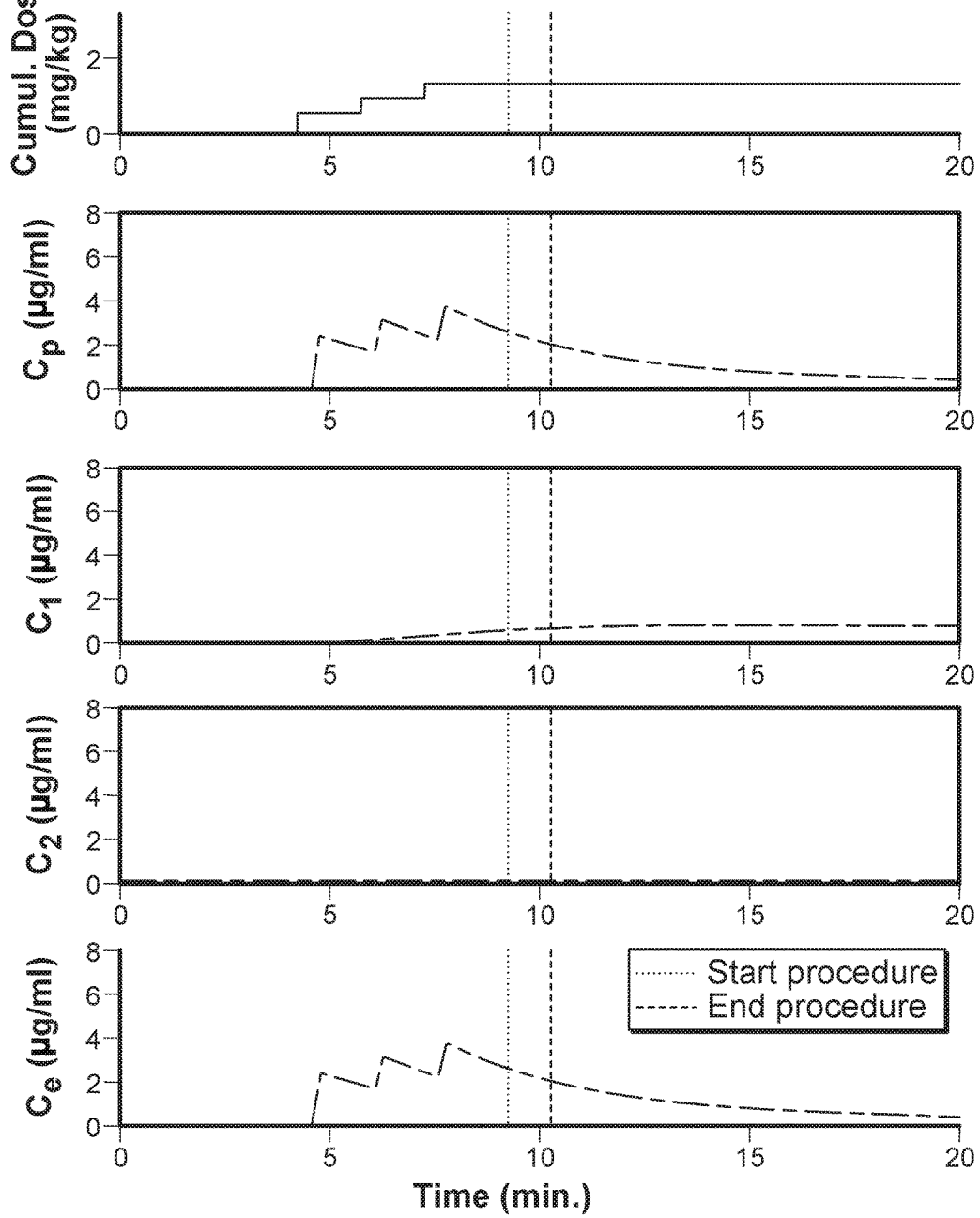
FIG. 20 displays the plasma- and effect-site concentrations estimated from a multi-compartment propofol sedation agent model proposed in the literature. The plasma concentration is observed to closely approximate the effect-site concentration, and the peripheral concentrations, $c_1$ and $c_2$, are comparatively small, according to an illustrative implementation of the disclosure.
Figure 21:
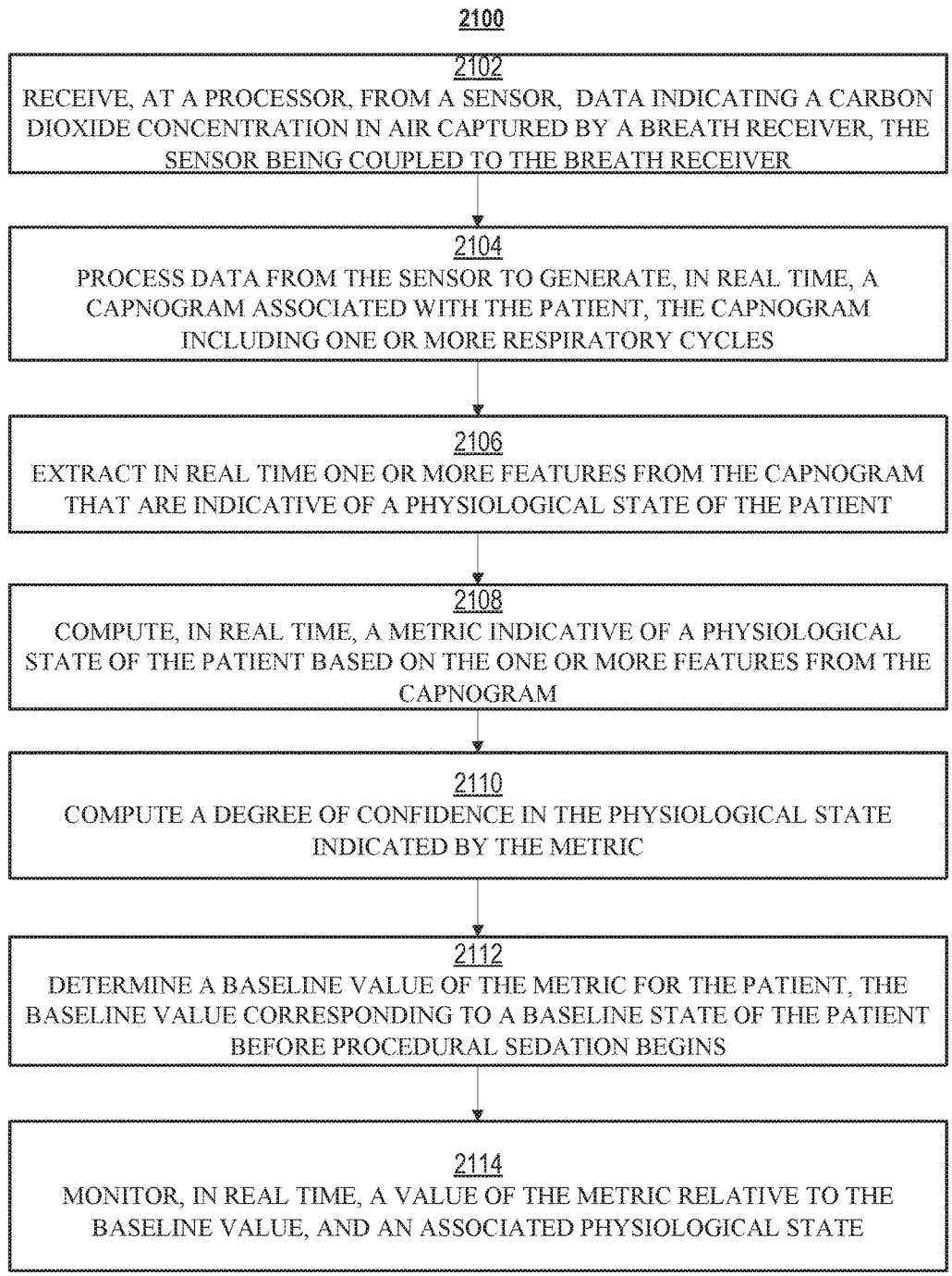
FIG. 21 is a flow chart depicting a method for automatically providing a quantitative assessment of a physiological state of a patient during procedural sedation, according to an illustrative implementation of the disclosure.

FIG. 20 displays the plasma- and effect-site concentrations estimated from a multi-compartment propofol sedation agent model proposed in the literature, according to an illustrative implementation of the disclosure. The parameters in the model are determined from values established in the literature, some of them age- and weight-dependent. Time is shown on the x-axis, which is the same for all plots in FIG. 20. The cumulative dose of sedative is shown on the y-axis in the top graph. The estimated concentration is shown in micrograms per milliliter on the y-axis for the remaining charts in FIG. 20. The second graph (the 'first' plot being the top plot) shows plasma concentration. The third and fourth graphs show peripheral concentrations, $c_2$ and $c_2$, e.g. concentrations in areas of the body besides the plasma. The bottom chart shows the effect-site concentration. The plasma concentration is observed to closely approximate the effect-site concentration, and the peripheral concentrations are comparatively small. This suggests that a simplified single-compartment model may instead be used to model both the plasma and effect-site concentrations during procedural sedation.

FIG. 21 is a flow diagram depicting a method 2100 for automatically providing a quantitative assessment of a physiological state of a patient during procedural sedation, according to an illustrative implementation of the disclosure. The method 2100 includes the steps of receiving, at a processor, from a sensor, data indicating a carbon dioxide concentration in air captured by a breath receiver, the sensor being coupled to the breath receiver (at step 2102), processing data from the sensor to generate, in real time, a capnogram associated with the patient, the capnogram including one or more respiratory cycles (at step 2104), extracting, in real time, one or more features from the capnogram that are indicative of a physiological state of the patient (at step 2106), computing, in real time, a metric indicative of a physiological state of the patient based on the one or more features from the capnogram (at step 2108), computing a degree of confidence in the physiological state indicated by the metric (at step 2110), determining a baseline value of the metric for the patient, the baseline value corresponding to a baseline state of the patient before procedural sedation begins (at step 2112), and monitoring, in real time, a value of the metric relative to the baseline value, and an associated physiological state (at step 2114).

At step 2102, data, measured by a sensor, indicating a carbon dioxide concentration in air captured by a breath receiver is received at a processor. The breath receiver is in fluid communication with a patient who is undergoing procedural sedation with a sedation agent (e.g. as described with reference to FIG. 2). The method 2100 may also use data associated with standard monitoring methods, including pulse oximetry, automated blood pressure measurement, respiratory rate, and visual assessment. One or more additional inputs may be EEG, auditory evoked potentials, galvanic skin (or electrodermal) response, pulse oximetry monitoring, breath gas monitoring, and electrocardiogram (ECG) monitoring. The method 2100 may incorporate other information such as patient data, medication type and dosage, physiological data (respiratory rate, oxygen saturation, heart rate, electrodermal response), procedural data, outputs from a pharmacokinetic, pharmacodynamic, or ventilatory model, or video recording. Demographic or clinical parameters obtained from procedural documentation may include age, weight, gender, procedure type, and medication data. Sedation scoring systems such as the Ramsay Sedation Scale, Sedation Agitation Scale, and Motor Activity Assessment Scale, among others, may be used in combination with the metric to correlate capnogram data with physiological states. In addition, physiological and/or procedural data may be used to assess a relative predictive value of signal monitoring. The patient may begin in an exemplary baseline state and may be anxious or agitated ahead of his/her procedure. The patient may be given sedatives or narcotics, a first drug administration, which changes the sedation state of the patient to a more cooperative, tranquil state, e.g., a "deeper" sedation state. The patient may then be given additional drug doses, which impact his/her sedation state, such that the patient responds to commands only, and subsequently responds only briefly to stimuli. The physician may decide to start the procedure once the patient is below a certain responsiveness threshold, indicated for example by the dashed line in FIG. 2

At step 2104, data from the sensor is processed to generate, in real time, a capnogram associated with the patient, the capnogram including one or more respiratory cycles. The data is received, from a sensor, at a processor, which processes the capnogram data (e.g. as discussed with reference to FIG. 9). In some implementations, the processing includes decimation of low-pass filtering to reduce noise and quantization effects. In some implementations, time domain analysis of the capnogram is utilized and includes detection of distinct exhalations by slope changes, determination of exhalation duration, end-exhalation slope, $ETCO_2$, determining time spent at $ETCO_2$, and curve length.

At step 2106, one or more features from the capnogram that are indicative of physiological state of the patient are extracted in real time (e.g. as discussed with reference to FIG. 9). The processor may extract capnogram features from the preprocessed capnogram data, including capnogram features such as $ETCO_2$, S1, S2, and S3, as described above. A frequency/spectral domain analysis of the capnogram data may be used, in combination with time domain analysis, to extract capnogram features. Spectral domain components, i.e., frequency domain analysis at prefixed or varying time intervals, may be extracted through at least one of short-time Fourier transforms, wavelet transforms, and power spectral density analyses. Spectral domain components may provide direct measures of localized signal variability and periodicity. The analytical methods may be parameterized by at least one of window size, hop length, and window shape. Extracted features include, but are not limited to, 95% spectral edge frequency or other measures of spectral extent, degree-of-periodicity indices, and discrete wavelet coefficients. Periodicity indices may provide information on the shape and regularity of patient breathing over a fixed duration of time. In some implementations, the processor causally median filters, for example by subtracting an approximate mean value and dividing by an approximate standard deviation, the time series capnogram data.

At step 2108, a metric indicative of a physiological state of the patient is computed based on the features of the capnogram (e.g. as described with reference to FIG. 10). In some implementations, the metric is computed based on features extracted from an exhalation, referred to as exhalation n, and preceding exhalations (numbered n−1, n−2, etc.), to determine a set of data clusters indicative of possible physiological states of the patient. In some implementations, a clustering technique is applied to the features. Each cluster may be represented by its centroid. As discussed with reference to FIG. 10, and throughout this disclosure, the metric may be a multi-parameter metric. The method 2100 may use the computed metric to associate exhalation n with one of the clusters in the cluster set which best represents the physiological state associated with exhalation n, based on the features of exhalation n. The current exhalation is assigned to a cluster. The assignment to a cluster may take into account, in addition to the value of the metric, information input from other patients, procedures, or physicians in the case of a semi-supervised or supervised learning technique. For example, additional data taken into account for clustering may include patient demographic and physiological data or indicators (e.g., age, weight, allergies, conditions) or a pharmacokinetic model and/or a pharmacodynamic model of drugs and procedural sedation agents, providing information on how the sedation agents or drugs propagate and affect sedation for a particular patient or patients in general.

The method 2100 may apply a clustering technique that computes a number of clusters, k, which may be specified by the user or determined by the clustering technique. A k-means clustering technique using the Euclidean distance metric may be implemented. The starting or initialization values for computation of the centroids at stage n may be the centroids determined at stage n−1. In an exemplary implementation, the clustering technique is a causal clustering technique which uses prior cluster information to guide the present clustering. The determination of the number of clusters, k, may be accomplished by requiring the intra-cluster separation of features to be small relative to the inter-cluster separation. The method 2100 may label or number the clusters, associating each determined cluster with a sedation state, sequentially. For example, the cluster associated with exhalations that preceded the first dose of procedural sedation agent may be labeled as the baseline state or "sedation state 0", and the clusters encountered sequentially in subsequent exhalations up to exhalation n may be numbered as sedation states 1 through k−1. In procedural sedation, k may be in the range of two to ten, depending on the patient or procedure, analogous to the qualitative rating of various subjective clinical sedation scales, such as the Ramsay Sedation Scale. For example, the Ramsay scale indicates that a patient at level 1 is anxious, agitated, restless; a patient at level 2 is cooperative, oriented, tranquil; a patient at level 3 responds only to verbal commands; a patient at level 4 is asleep, with a brisk response to light stimulation; a patient at level 5 is asleep, with a sluggish response to stimulation; and a patient at level 6 is unarousable. Alternatively, other scales such as the Richmond Agitation and Sedation Score (RASS) or the Riker Sedation-Agitation Scale (SAS) provide scores from −5 to +4, and from 1 to 7, respectively, both going from dangerous agitation to unarousable.

In an embodiment, an unsupervised learning technique other than a k-means clustering technique may be used. For example, mixture models or hierarchical clustering may be used. Alternatively, expectation-maximization techniques, principal component analysis, independent component analysis, singular value decomposition or any other causal technique may be used.

In an embodiment, a semi-supervised or supervised learning technique may be used, with a physician providing input on part of the data, e.g., labeling certain features or data from a patient. Machine learning may take place with data collected on a single patient undergoing a single procedure, but machine learning may also take place with data collected on a single patient over multiple procedures, or multiple patients undergoing a variety of procedures. A training stage, testing stage and application stage may be used for the machine learning, similar, for example, to the training, testing and application stages described in FIGS. 2-5 of U.S. application Ser. No. 13/849,284 for example.

In an exemplary embodiment, a set of three (i.e., k=3) clusters and associated centroids may be found at stage n, using information from the current and past exhalations. Centroid separation metrics for use in evaluation of the quality of clustering or choice of k may include centroid triangle area in the case where k=3 (or the analogous centroid simplex volume for k>3) and average intercentroid distance. The centroid triangle area is hereby defined as the area of the triangle with vertices located at the three centroids in the plane defined by those centroids. Average intercentroid distance is hereby defined as the average Euclidean distance between each pair of centroids. In this exemplary embodiment where k=3 the three clusters may be labeled as the "baseline state," "sedation state 1" and "sedation state 2," sequentially.

At step 2110, a degree of confidence in the physiological state indicated by the metric is computed. In some implementations, the method 2100 computes the measure of confidence in the assignment of exhalation n to a particular cluster, based on the relative distances of the features of this exhalation from the various clusters, as determined by the metric computed at step 2108.

At step 2112, a baseline value of the metric for the patient, which corresponds to a baseline state of the patient before procedural sedation begins is determined. As discussed with reference to FIG. 10, in some implementations, in the event that the first dose has not yet been administered, the method 2100 assigns the current physiological state as the baseline state.

At step 2114, a value of the metric relative to the baseline value and an associated physiological state relative to the baseline are monitored in real time. The method 2100 may operate in real time on capnogram data collected continuously. In an illustrative implementation, as discussed with reference to FIG. 10 (e.g. steps 1014-1020), a state change, i.e., a change in the state of sedation of the patient may be confirmed after three consecutive exhalations are assigned to the same new cluster, i.e., after the patient has been in a new state of sedation for at least three exhalations. The method 2100 may determine whether the cluster selected for exhalation n is the same as the cluster for exhalation n−3. In the event that the cluster for exhalation n is the same as the cluster of exhalation n−3, the physiological state assigned to exhalation n is the same as the physiological state assigned to exhalation n−3, and the method 2100 repeats the step for the next exhalation. In the event that the cluster for exhalation n and the physiological state corresponding to exhalation n is different from the cluster and corresponding physiological state for exhalation n−3, the method 2100 checks whether the cluster for exhalation n is also different from the cluster for exhalation n−2 and exhalation n−1. If the cluster for exhalation n is not the same as the cluster for exhalation n−2 or exhalation n−1, there is no change in physiological state. Alternatively, if the cluster for exhalation n is the same as the cluster for exhalation n−2 and exhalation n−1, a new sedation state may be assigned. The resulting physiological state may be labeled according to when it occurs during the procedural sedation. For example, the patient's state before the first drug administration is labeled as "Baseline." Subsequent states may be labeled "Sedation1" and "Sedation2" in sequential order, for example. The clustering technique assigns each exhalation into a cluster corresponding to a sedation state and corresponding patient sedation level. As noted above, assignment to a cluster may be based on the value of the metric relative to the baseline and additional information such as demographic and physiological data about the patent undergoing procedural sedation, or information from other patients and other procedures.

FIG. 22 is a flow diagram depicting a method 2200 for automatically guiding procedural sedation, according to an illustrative implementation of the disclosure. The method 2200 includes the steps of identifying sedation agent information including at least one of a time, a type, and an amount of sedation agent administered to a patient (at step 2202), computing, using a pharmacokinetic model, a concentration of sedation agent in the body of the patient based on the sedation agent information (at step 2204), computing a first predicted sedation level based on the computed concentration (at step 2206), selecting a candidate dose of sedation agent based on the sedation agent information (at step 2208), computing a second predicted sedation level based on the candidate dose of sedation agent (at step 2210), and providing, to a display, at least one of the computed concentration and the first predicted sedation level and at least one of the candidate dose of sedation agent and the second predicted sedation level (at step 2212).

At step 2202, sedation agent information including at least one of a time, a type, and an amount of sedation agent administered to a patient is identified. The sedation agent information may be recorded through a suitable user interface by a clinician, recorded by a smart infusion or administration device (e.g. a device such as a pump that is configured to record the time and amount of sedation agent the device delivers to a patient), or any suitable means. In some implementations, an interactive bedside monitor is configured to record sedation agent information.

At step 2204, a concentration of sedation agent in the body of the patient is computed, using a pharmacokinetic model, based on the sedation agent information. As discussed with reference to an illustrative implementation shown in FIG. 19, a simplified single-compartment model may be used to estimate plasma concentration of sedation agent following an input of sedation agent administration amounts and times, according to an illustrative implementation of the disclosure. In some implementations, the sedation agent is administered in discrete boluses. A first order differential equation may be used to solve for the plasma concentration as a function of time is shown below the model. The equation relates the rate of change in plasma concentration to plasma concentration $c_p(t)$, bolus administration input dosing information as a function of time $u(t)$, plasma volume $V_1$, and a rate constant $k_w$, describing clearance of the sedation agent from the plasma in the following manner: $\dot{c}_p(t) = -k_{10} * c_p(t) + 1/V_1 * u(t)$. The parameters such as plasma volume and $k_{10}$ may be age and gender specific. Bolus doses are administered at times and in doses reflected by the bolus administration input. The cumulative dose may be a step function of mg/kg of drug administered as a function of time or any suitable input function, including possibly a continuous function of time. The plasma volume represents the plasma volume of the patient. The elimination constant reflects the rate at which the drug is expected to be eliminated from the compartment, the plasma, in the model. Nominal values of the parameter $V_1$, which is plasma volume, are tabulated for different weights and age groups. The parameter $k_{10}$, which represents elimination rate of the drug from plasma, is known in the literature from experiments. The pharmacokinetic model may use parameters including age, weight, height, lean body mass, gender, and procedure type to determine the values for variables (e.g. the elimination constant) and to compute a predicted concentration. As discussed with reference to FIG. 20, the plasma concentration may be used to closely approximate the effect-site concentration. This suggests that a simplified single-compartment model may instead be used to model both the plasma and effect-site concentrations during procedural sedation. In some implementations, a multiple compartment model, or any suitable pharmacokinetic model, may be used to compute the concentration of the sedation agent in the patient's body. In some implementations, the systems and methods of the present disclosure are configured to alert a user when any computed concentration exceeds a first concentration threshold or is below a second concentration threshold. The thresholds may be user configured, e.g. through an interactive bedside monitor, or configured according to clinical guidelines.

At step 2206, a first predicted sedation level is computed based on the concentration computed in step 2204. As discussed with reference to FIG. 15, the continuously estimated effect-site concentration of sedation agent may be used to predict whether the Ramsay Sedation Score of the patient exceeds a threshold. In some implementations, a pharmacodynamic model is used to compute the predicted sedation level based on the output of the pharmacokinetic model. In some implementations, the systems and methods of the present disclosure are configured to alert a user when the computed concentration exceeds a first concentration threshold or is below a second concentration threshold. The thresholds may be user configured, e.g. through an interactive bedside monitor. In some implementations, the systems and methods of the present disclosure are configured to alert a user when any computed sedation exceeds a first sedation threshold or is below a second sedation threshold. The thresholds may be user configured, e.g. through an interactive bedside monitor, or configured according to clinical guidelines.

At step 2208, a candidate dose of sedation agent is selected based on the sedation agent information. In some implementations, the candidate dose of sedation agent is selected to represent a bolus of sedation agent that may be administered at a given time. In some implementations, the candidate dose will be identical to the last administered dose, the average size of the doses administered during the sedation, or otherwise based on the previously administered doses. In some implementations, the candidate dose will be input by a clinician, e.g. into an interface in an interactive bedside monitor. In some implementations, the candidate dose will be calculated by a processor using a pharmacodynamic model to achieve a target effect-site concentration.

At step 2210, a second predicted sedation level is computed based on the candidate dose of sedation agent. In some implementations, similarly to step 2204, a pharmacokinetic model is used to compute a second predicted concentration based on the candidate dose of sedation agent. Similarly to step 2206, the second predicated concentration is used to determine a second predicted sedation level.

At step 2212, at least one of the computed concentration and the first predicted sedation level and at least one of the candidate titration of sedation agent and the second predicted sedation level are provided to a display. In some implementations, the display is an interactive bedside monitor, and the display of candidate doses and predicted sedation levels is used to guide the dosing and timing of sedation agent.

While various embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

What is claimed is:

1. A system for automatically providing a quantitative assessment of a physiological state of a patient during procedural sedation, the system comprising:
 a breath receiver in fluid communication with a patient undergoing procedural sedation;
 a sensor configured to measure a carbon dioxide concentration in air captured by the breath receiver, the sensor being coupled to the breath receiver;
 a processor configured to:
  generate, in real time, a capnogram associated with the patient, the capnogram being generated based on the carbon dioxide concentration measured by the sensor over one or more respiratory cycles;
  extract, in real time, one or more features from the capnogram that are indicative of the physiological state of the patient;
  determine, in real time, using a clustering technique, clusters of the one or more features indicative of the physiological state of the patient, wherein each of the clusters corresponds to a different physiological state;
  compute, in real time, a metric indicative of the physiological state of the patient based, at least in part, on the determined clusters;
  determine a baseline value of the metric for the patient, the baseline value corresponding to a baseline physiological state of the patient before procedural sedation begins; and
  monitor, in real time, a value of the metric relative to the baseline value to assess the physiological state of the patient during the procedural sedation, wherein monitoring the value of the metric relative to the baseline value comprises determining the physiological state of the patient based, at least in part, on the determined clusters; and
 a display configured to display an indication of the assessed physiological state of the patient during the procedural sedation.

2. The system of claim 1, wherein the processor is further configured to:
 detect in real time a change in the value of the metric over at least two respiratory cycles; and
 determine in real time a change in the physiological state of the patient based on the change in the value of the metric.

3. The system of claim 2, wherein the processor is further configured to:
 correlate the physiological state of the patient with one or more physiological data or indicators to determine an accuracy of the determined change in physiological state.

4. The system of claim 3, wherein the one or more physiological data or indicators are input to the clustering technique and include at least one of physiological data provided by a user, outputs from at least one of a pharmacokinetic, pharmacodynamic, and ventilatory model, and a score on a qualitative sedation scoring scheme.

5. The system of claim 1, wherein the extracting the one or more features includes fitting a portion of the capnogram to a parameterized function.

6. The system of claim 1, wherein the one or more features include a measure of periodicity of the capnogram.

7. The system of claim 1, wherein the one or more features include the output of at least one of a pharmacokinetic model, a pharmacodynamics model, and a ventilatory model.

8. The system of claim 1, wherein the one or more features that are indicative of the physiological state of the patient include a terminal value of the carbon dioxide concentration on exhalation, an end-exhalation slope, and a ratio of an intermediate exhalation slope over an initial exhalation slope.

9. The system of claim 1, wherein the clustering technique is a k-means technique, with a number "k" of clusters corresponding to a number of sedation states for the patient.

10. The system of claim 1, wherein the clustering technique is a technique with a variable number of clusters.

11. The system of claim 1, wherein the metric is a multi-parameter metric, where the multi-parameter metric indicates a separation from a cluster centroid.

12. The system of claim 11, wherein a closest centroid, as determined by the multi-parameter metric, is indicative of the physiological state of the patient.

13. The system of claim 11, wherein a separation from a nearest centroid relative to a separation from a next-closest centroid is indicative of a degree of confidence in the physiological state of the patient.

14. The system of claim 1, wherein the physiological state of the patient pertains to a sedation level.

15. A method for automatically providing a quantitative assessment of a physiological state of a patient during procedural sedation, the method comprising:

receiving, at a processor, from a sensor, data indicating a carbon dioxide concentration in air captured by a breath receiver, the sensor being coupled to the breath receiver;

generating, in real time, a capnogram associated with the patient, the capnogram being generated based on the carbon dioxide concentration measured by the sensor over one or more respiratory cycles;

extracting, in real time, one or more features from the capnogram that are indicative of a physiological state of the patient;

determining, in real time, using a clustering technique, clusters of the one or more features indicative of the physiological state of the patient, wherein each of the clusters corresponds to a different physiological state;

computing, in real time, a metric indicative of a physiological state of the patient based, at least in part, on the determined clusters;

determining a baseline value of the metric for the patient, the baseline value corresponding to a baseline physiological state of the patient before procedural sedation begins; and monitoring, in real time, a value of the metric relative to the baseline value to assess the physiological state of the patient during the procedural sedation, wherein monitoring the value of the metric relative to the baseline value comprises determining the physiological state of the patient based, at least in part, on the determined clusters; and displaying an indication of the assessed physiological state of the patient during the procedural sedation.

* * * * *